(12) United States Patent
Hillukka et al.

(10) Patent No.: US 9,021,674 B2
(45) Date of Patent: May 5, 2015

(54) SYSTEM FOR LOADING A COLLAPSIBLE HEART VALVE

(75) Inventors: Brett Allen Hillukka, Hanover, MN (US); Huisun Wang, Maple Grove, MN (US); Valerie J. Glazier, Eden Prairie, MN (US); Yousef F. Alkhatib, Edina, MN (US); Jacob John Daly, Blaine, MN (US); Ralph Joseph Thomas, Champlin, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 40 days.

(21) Appl. No.: 13/364,501

(22) Filed: Feb. 2, 2012

(65) Prior Publication Data

US 2012/0330408 A1 Dec. 27, 2012

Related U.S. Application Data

(60) Provisional application No. 61/438,812, filed on Feb. 2, 2011, provisional application No. 61/449,893, filed on Mar. 7, 2011, provisional application No. 61/512,637, filed on Jul. 28, 2011.

(51) Int. Cl.
*B25B 31/00* (2006.01)
*B23P 11/00* (2006.01)
(Continued)

(52) U.S. Cl.
CPC ............ *A61F 2/2427* (2013.01); *A61F 2/0095* (2013.01); *A61F 2/2436* (2013.01);
(Continued)

(58) Field of Classification Search
CPC ......... H02G 3/22; H02G 3/00; H02G 3/0443; H02G 1/00; B23Q 3/00
USPC ............... 29/270, 244, 255, 261, 278; 254/134.3 FT, 134.4 R
See application file for complete search history.

(56) References Cited

U.S. PATENT DOCUMENTS 3,657,744 A   4/1972   Ersek
4,423,730 A   1/1984   Gabbay
(Continued)

FOREIGN PATENT DOCUMENTS

EP   1129744 A1   9/2001
EP   1157673 A2   11/2001
(Continued)

OTHER PUBLICATIONS

International Search Report for Application No. PCT/US2012/048298 dated Nov. 7, 2012.
(Continued)

*Primary Examiner* — Lee D Wilson
(74) *Attorney, Agent, or Firm* — Lerner, David, Littenberg, Krumholz & Mentlik, LLP

(57) ABSTRACT

An assembly for collapsing a self-expanding prosthetic heart valve includes a compression member, a support member and a constricting member. The compression member has a tapered wall between its first open end and its second open end, the tapered wall defining an open space adapted to receive the valve. The support member has a base and a recess adapted to receive an end of the valve. The support member and the compression member are movable toward one another to compress the valve and push it through a relatively small aperture in the second open end of the compression member. The second end of the constricting member is sized to receive the compressed valve from the second open end of the compression member for loading into a delivery device.

20 Claims, 25 Drawing Sheets

(51) Int. Cl.
  *A61F 2/24* (2006.01)
  *A61F 2/00* (2006.01)
  *A61F 2/97* (2013.01)
  *A61F 2/95* (2013.01)

(52) U.S. Cl.
  CPC ............. *A61F 2/2412* (2013.01); *A61F 2/97* (2013.01); *A61F 2002/9522* (2013.01); *A61F 2250/0039* (2013.01)

(56) References Cited

U.S. PATENT DOCUMENTS

| | | | |
|---|---|---|---|
| 5,843,167 A | 12/1998 | Dwyer et al. | |
| 5,924,424 A | 7/1999 | Stevens et al. | |
| 5,968,068 A | 10/1999 | Dehdashtian et al. | |
| 6,077,297 A | 6/2000 | Robinson et al. | |
| 6,132,458 A * | 10/2000 | Staehle et al. | 623/1.11 |
| 6,306,141 B1 | 10/2001 | Jervis | |
| 6,471,718 B1 * | 10/2002 | Staehle et al. | 623/1.11 |
| 6,623,518 B2 | 9/2003 | Thompson et al. | |
| 6,814,746 B2 | 11/2004 | Thompson et al. | |
| 6,830,584 B1 | 12/2004 | Seguin | |
| 6,935,389 B2 | 8/2005 | Rinaldi | |
| 7,014,074 B1 | 3/2006 | Rinaldi | |
| 7,018,406 B2 | 3/2006 | Seguin et al. | |
| 7,311,730 B2 | 12/2007 | Gabbay | |
| 7,510,572 B2 | 3/2009 | Gabbay | |
| 7,682,390 B2 | 3/2010 | Seguin | |
| 7,803,185 B2 | 9/2010 | Gabbay | |
| 8,561,967 B2 * | 10/2013 | Hendriksen et al. | 254/134.3 FT |
| 8,585,019 B2 * | 11/2013 | Melsheimer et al. | 254/134.3 R |
| 2003/0050694 A1 | 3/2003 | Yang et al. | |
| 2003/0070682 A1 | 4/2003 | Wilson et al. | |
| 2004/0210304 A1 | 10/2004 | Seguin et al. | |
| 2005/0137695 A1 | 6/2005 | Salahieh et al. | |
| 2005/0137697 A1 | 6/2005 | Salahieh et al. | |
| 2005/0194578 A1 * | 9/2005 | Morris | 254/134.3 FT |
| 2006/0074484 A1 | 4/2006 | Huber | |
| 2006/0106415 A1 | 5/2006 | Gabbay | |
| 2006/0142848 A1 | 6/2006 | Gabbay | |
| 2006/0167468 A1 | 7/2006 | Gabbay | |
| 2006/0259120 A1 | 11/2006 | Vongphakdy et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0073391 A1 | 3/2007 | Bourang et al. | |
| 2007/0088431 A1 | 4/2007 | Bourang et al. | |
| 2007/0112422 A1 | 5/2007 | Dehdashtian | |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0239271 A1 | 10/2007 | Nguyen | |
| 2007/0244552 A1 | 10/2007 | Salahieh et al. | |
| 2007/0270931 A1 * | 11/2007 | Leanna et al. | 623/1.11 |
| 2007/0270932 A1 * | 11/2007 | Headley et al. | 623/1.11 |
| 2008/0071369 A1 | 3/2008 | Tuval et al. | |
| 2008/0147182 A1 | 6/2008 | Righini et al. | |
| 2008/0221703 A1 | 9/2008 | Que et al. | |
| 2009/0054975 A1 | 2/2009 | del Nido et al. | |
| 2009/0093876 A1 | 4/2009 | Nitzan et al. | |
| 2009/0143857 A1 | 6/2009 | Melsheimer et al. | |
| 2010/0004740 A1 | 1/2010 | Seguin et al. | |
| 2010/0051886 A1 * | 3/2010 | Cooke et al. | 254/134.3 R |
| 2010/0286768 A1 | 11/2010 | Alkhatib | |
| 2010/0298931 A1 | 11/2010 | Quadri et al. | |
| 2011/0224678 A1 | 9/2011 | Gabbay | |
| 2012/0078352 A1 | 3/2012 | Wang et al. | |
| 2012/0330408 A1 * | 12/2012 | Hillukka et al. | 623/2.11 |

FOREIGN PATENT DOCUMENTS

| | | |
|---|---|---|
| WO | 2007071436 A2 | 6/2007 |
| WO | 2007081940 A2 | 7/2007 |
| WO | 2008070797 A2 | 6/2008 |
| WO | 2009/091509 A1 | 7/2009 |
| WO | 2010014834 A1 | 2/2010 |
| WO | 2010051025 A1 | 5/2010 |
| WO | 2010087975 A1 | 8/2010 |
| WO | 2010096176 A1 | 8/2010 |
| WO | 2012023979 A2 | 2/2012 |
| WO | 2012036742 A2 | 3/2012 |
| WO | 2012036744 A2 | 3/2012 |
| WO | 2012057983 A1 | 5/2012 |
| WO | 2012106491 A1 | 8/2012 |

OTHER PUBLICATIONS

International Search Report for Application No. PCT/US2012/048307 dated Feb. 28, 2013.

Quaden et al., "Percutaneous aortic valve replacement: resection before implantation", pp. 836-840, European J. of Cardio-thoracic Surgery, 27 (2005).

International Search Report and Written Opinion for Application No. PCT/US2012/023576 dated Jul. 6, 2012.

Overview of PRE-CE Mark Transcatheter Aortic Valve Technologies (powerpoint—dated Jun. 1, 2010).

International Search Report for Application No. PCT/US2011/001598 dated Jul. 6, 2012.

* cited by examiner

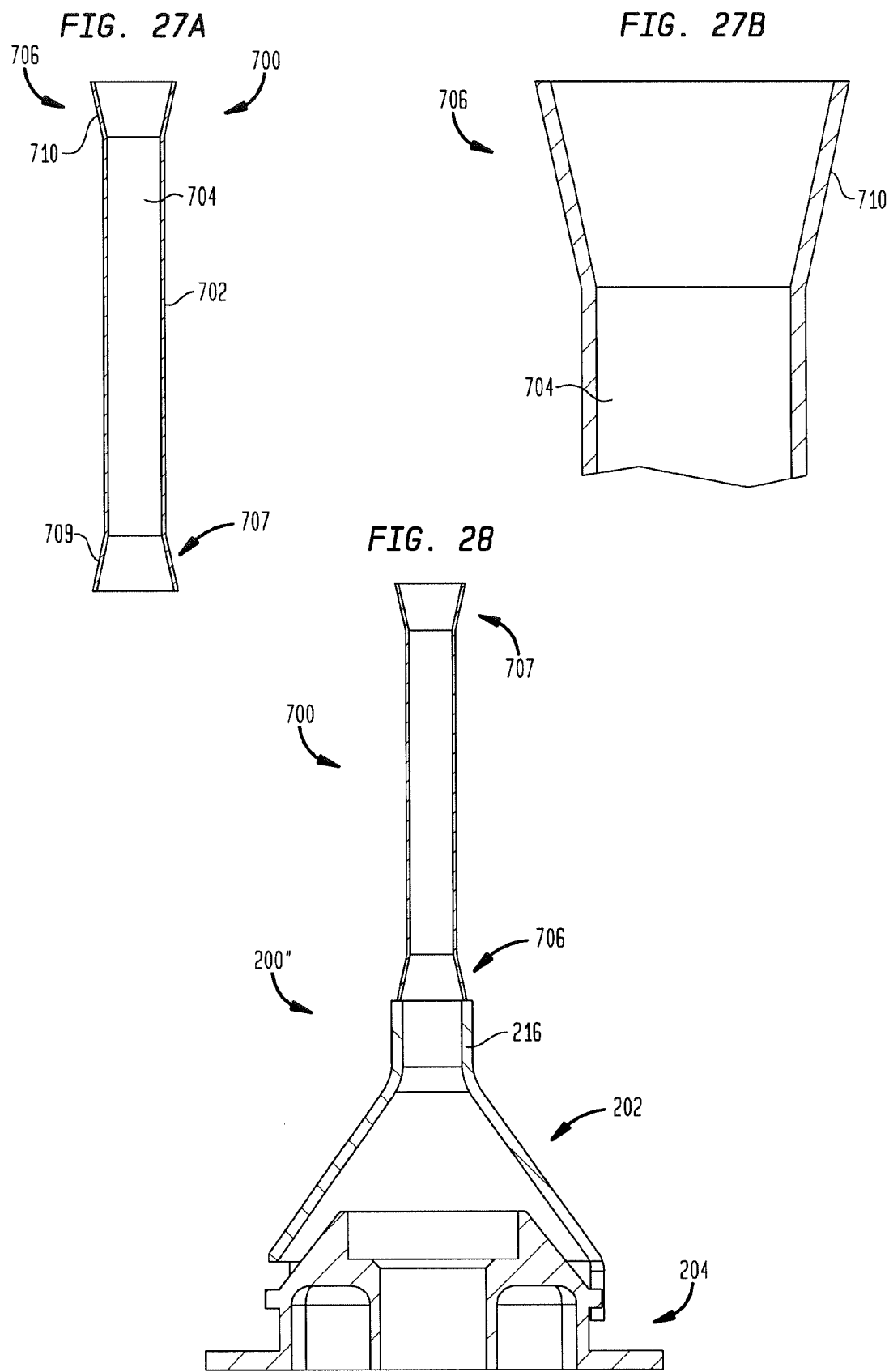

SYSTEM FOR LOADING A COLLAPSIBLE HEART VALVE

CROSS-REFERENCE TO RELATED APPLICATIONS

This application claims the benefit of the filing date of U.S. Provisional Patent Application Nos. 61/438,812, filed Feb. 2, 2011; 61/449,893, filed Mar. 7, 2011; and 61/512,637, filed Jul. 28, 2011, the disclosures of which are hereby incorporated herein by reference.

BACKGROUND OF THE INVENTION

The present disclosure relates to prosthetic heart valve implantation and, more particularly, to assemblies and methods for loading a self-expanding collapsible heart valve into a delivery device.

Prosthetic heart valves may be formed from biological materials such as harvested bovine valves or pericardial tissue. Such valves are typically fitted within a stent, which may be inserted into the heart at the annulus of the compromised native valve to replace the native valve. To perform such insertion procedure using a minimally invasive technique, it is typically necessary to compress the stent to a reduced diameter for loading into the delivery device.

In the case of valves formed from biological materials, the stented valve is preferably preserved in the open condition for storage as compression of the valve material for extended periods compromises the integrity of the biological valve. It is therefore necessary to crimp the valve, or reduce its diameter for loading in the delivery device, in the operating arena.

Present crimping devices and methods for collapsing a stented valve, including direct radial assemblies, have proven to be unsatisfactory as they include bulky assemblies, are difficult to master, are time consuming, impart undue stress on the stented valve, or exhibit other undesirable qualities. Moreover, it is sometimes difficult to securely engage the stent to the retaining element of a delivery device. It would therefore be beneficial to provide a device and method for collapsing a stented bioprosthetic heart valve using apparatus and techniques that overcome the deficiencies of conventional devices. In addition, such devices and methods could be useful in the loading of the collapsed stented valve into a minimally invasive delivery device.

BRIEF SUMMARY OF THE INVENTION

One aspect of the present invention provides assemblies for loading a self-expanding prosthetic heart valve into a delivery device. The assembly may include a compression member having a longitudinal axis, a first open end with a first diameter, a second open end with a second diameter less than the first diameter, and a wall which decreases in diameter from the first open end to the second open end, the wall defining an open space adapted to receive the valve; a support member having a longitudinal axis, a base and a recess extending along the longitudinal axis and adapted to receive an end of the valve, the support member and the compression member being movable relative to one another between an initial position in which the base of the support member is relatively far from the first open end of the compression member and an operative position in which the base of the support member is relatively close to the first open end of the compression member, wherein movement of the support member and the compression member from the initial position to the operative position pushes the valve through the open space such that the valve is radially compressed by the wall of the compression member as the valve advances through the open space; and a constricting member having a first end and a second end, the second end of the constricting member being sized to receive the compressed valve from the second open end of the compression member.

The constricting member may include an elongated tubular portion between the first end and the second end, and the elongated tubular portion may have a lumen sized to slidably receive at least a distal sheath of the delivery device. The constricting member may further include an end member on the second end, the end member having a free end and another end connected to the tubular portion, the lumen of the tubular portion having a substantially constant diameter, and the end member having a first diameter at the free end, a second diameter less than the first diameter at the another end, and a wall decreasing in diameter from the free end to the another end. Alternatively, the constricting member may further include an end member on the first and second ends thereof, each end member having a free end and another end connected to the tubular portion, the lumen of the tubular portion having a substantially constant diameter, and each end member having a first diameter at the first end, a second diameter less than the first diameter at the another end, and a wall decreasing in diameter from the free end to the another end.

The assembly may further include a tubular extension on the second open end of the compression member, the tubular extension having a lumen therethrough, the tubular extension being engaged with the end member of the constricting member; and a first seal interposed between the end member of the constricting member and the tubular extension of the compression member. The seal may include an O-ring. Further, the tubular extension may include an annular groove, and the seal may be positioned in the annular groove. Alternatively, the end member of the constricting member may include an annular groove, and the seal may be positioned in that annular groove. The assembly also may include a second seal disposed in the lumen of the elongated tubular portion of the constricting member. That seal also may include an O-ring. In addition, the lumen of the elongated tubular portion of the constricting member may include an annular groove, and the another seal may be positioned therein.

The constricting member may include a plurality of interlocking segments connected to one another, each of the interlocking segments having a first end with a first diameter, a second end with a second diameter greater than the first diameter, and a wall increasing in diameter from the first end to the second end, the interlocking segments being connected together in series with the second end of one interlocking segment connected to the first end of the next adjacent interlocking segment. The diameter of the wall may increase in a step-wise fashion, or may increase uniformly from the first end to the second end.

The assembly may further include at least one tear line extending in a longitudinal direction between the first end and the second end of the constricting member for splitting the constricting member in the longitudinal direction. The constricting member may include a second tear line spaced from the at least one tear line for peeling a portion of the constricting member between the tear lines away from a remainder of the constricting member. A tab may extend from the portion of the constricting member between the tear lines for peeling the portion of the constricting member from the remainder of the constricting member.

The assembly may further include a locking assembly for locking the compression member to the support member. The locking assembly may include a male connecting member on one of the support member or the compression member, and a female connecting member on the other of the support member or the compression member for mating with the male connecting member. The male connecting member may include a plurality of pins extending in radial directions from the longitudinal axis of the one of the support member or the compression member, and the female connecting member may include a plurality of features on the other of the support member or the compression member adapted to mate with the plurality of pins. Alternatively, the female connecting member may include an annular groove extending along an inner surface of the first open end of the compression member, and the male connecting member may include a plurality of locking tabs on the support member adapted to engage the annular groove of the compression member so as to connect the support member to the compression member.

In yet another alternative, the male connecting member may include an annular rim extending from the first open end of the compression member, and the female connecting member may include an annular slot on the support member sized to receive the rim so as to connect the compression member to the support member. In a still further alternative, the locking assembly may include a bead extending along an outer periphery of the first open end of the compression member and locking tabs on the support member, the locking tabs being configured to engage the bead of the compression member so as to connect the support member to the compression member.

Another aspect of the present invention provides methods for loading a self-expanding prosthetic heart valve into a delivery device. The delivery device may include a tip, a retaining element, a compartment defined between the tip and the retaining element and adapted to receive the heart valve, and a distal sheath movable between a closed position fully covering the compartment and an open position uncovering the compartment. The heart valve may include a stent, a valve assembly supported by the stent, and at least one retainer at one end of the stent, the heart valve having an expanded condition and a collapsed condition.

Methods according to this aspect of the present invention may include inserting the heart valve in the expanded condition into a compression member having an inner surface which decreases in diameter uniformly from a first open end to a second open end; advancing the heart valve through the compression member until the at least one retainer protrudes from the second open end of the compression member; positioning the delivery device in an initial position in a constricting member, the constricting member having a first end, a second end and an elongated tubular portion between the first end and the second end, the delivery device in the initial position having the distal sheath in the open position and the retaining element positioned outside the constricting member; attaching the at least one retainer of the heart valve to the retaining element of the delivery device; and moving the distal sheath of the delivery device to the closed position during which the heart valve is advanced through the second open end of the compression member and into the elongated tubular portion of the constricting member to place the heart valve in the collapsed condition.

The method may further include filling at least a portion of the compression member with a sterile liquid before moving the distal sheath of the delivery device to the closed position to remove air from the heart valve and the delivery device. The air removal step may include agitating the sterile liquid in the compression member, moving a probe in the sterile liquid between the cuff and the leaflets of the heart valve, and/or moving a syringe in the sterile liquid adjacent the retaining element of the delivery device. A sterile liquid may also be used to remove air from the tubular outer shaft between the retaining element and an operating handle of the delivery device.

In an alternate method, the distal sheath of the delivery device and the heart valve may be submerged into a container holding the sterile liquid to remove air from the heart valve and the delivery device before moving the distal sheath of the delivery device to the closed position. Shaking or tapping the submerged delivery device and the heart valve may assist in removing the air therefrom.

BRIEF DESCRIPTION OF THE DRAWINGS

Various embodiments of the present loading assembly are disclosed herein with reference to the drawings, wherein:

FIG. 27A is a longitudinal cross-sectional view of a constricting member in accordance with a further embodiment of the present invention;

FIG. 27B is an enlarged longitudinal cross-sectional view of an end section of the constricting member of FIG. 27A;

FIG. 28 is a longitudinal cross-sectional view of a loading assembly in accordance with an embodiment of the present invention, including the compression member of FIG. 5, the support member of FIG. 6, and the constricting member of FIG. 27A;

DETAILED DESCRIPTION

Figure 1:
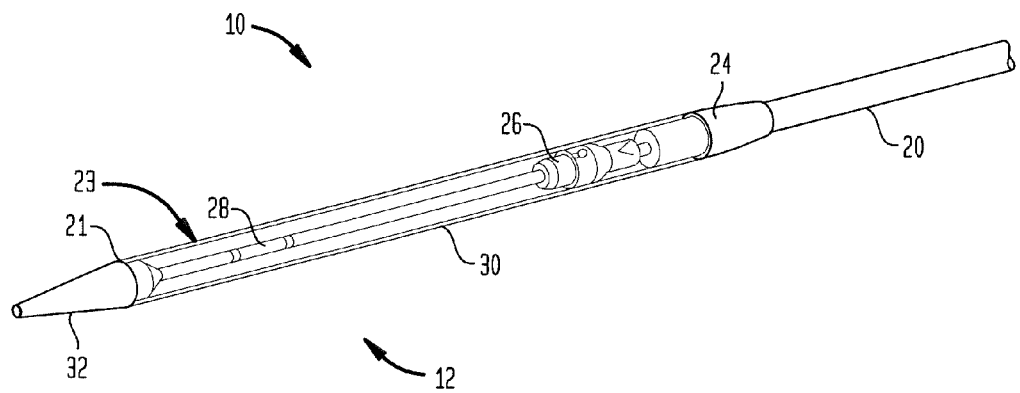
FIG. 1 is a perspective view of a distal portion of a delivery device.

Embodiments of the presently disclosed loading assemblies are described herein in detail with reference to the drawing figures, wherein like reference numerals identify similar or identical elements. In the drawings and in the description which follows, the term "proximal" refers to the end of the loading assembly, or portion thereof, which is closest to the operator in use, while the term "distal" refers to the end of the loading assembly, or portion thereof, which is farthest from the operator in use.

The present disclosure relates to assemblies and methods for loading a self-expanding stent or a collapsible prosthetic heart valve into a minimally invasive delivery device. An exemplary minimally invasive delivery device 10 is illustrated in FIGS. 1 and 2.

Figure 2:
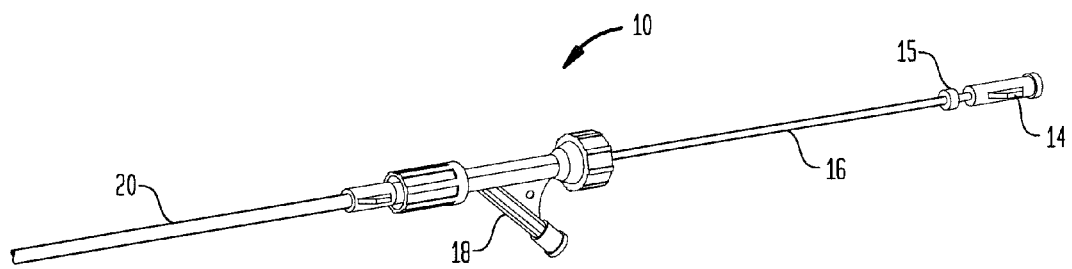
FIG. 2 is a perspective view of a proximal portion of the delivery device of FIG. 1.

As seen in FIGS. 1 and 2, an exemplary delivery device 10 for transfemoral delivery of a collapsible prosthetic heart valve (or other types of self-expanding collapsible stents) has a catheter assembly 12 for delivering the heart valve to and deploying the heart valve at a target location. The catheter assembly 12 includes a compartment 23 defined between an atraumatic tip 32 of the delivery device 10 and a retaining element 26. A support shaft 28 is connected between tip 32 and retaining element 26 and defines the length of compartment 23. A distal sheath 30 is slidably arranged relative to the compartment 23 so that, in a distalmost or closed position in which the distal end 21 of the sheath abuts atraumatic tip 32, the sheath covers the prosthetic heart valve and retains it for delivery to the target site, and in a proximal or open position in which the distal end 21 of the sheath is spaced from the atraumatic tip 32, the sheath uncovers the prosthetic heart valve for deployment at the target site.

An inner tube 16 having a lumen therethrough extends from a hub 14 at or near its proximal end to a distal end which may be connected to retaining element 26. Optionally, the distal end of inner tube 16 may extend through retaining element 26 and support shaft 28 for connection to atraumatic tip 32. In either arrangement, the distal end of inner tube 16 is connected to compartment 23 so as to define a fixed distance between hub 14 and the compartment. The lumen through inner tube 16 is sized to slidingly receive a guidewire (not shown) for use in guiding the delivery device to the target site. At its proximal end, inner tube 16 may be provided with a hemostasis valve (not shown) for preventing, or at least hindering, blood flow out from the inner tube.

Hub 14 is adapted for connection to another system or mechanism, such as an operating handle (not shown) for displacing the distal sheath 30. Mechanisms for displacing the distal sheath 30 between its proximal and distal positions are described in International Patent Application Publication No. WO/2009/091509, the disclosure of which is hereby incorporated by reference herein. A retaining ring 15 may be mounted on the inner tube 16 near hub 14.

Catheter assembly 12 further includes an outer shaft 20 which is connected at its distal end through a tapered transition member 24 to the proximal end of distal sheath 30, and at its proximal end to the operating handle (not shown). A Y-connector 18 may also be connected at the proximal end of outer shaft 20, and may include a hemostasis valve for hindering blood flow out from between the inner tube 16 and the outer shaft 20. The Y-connector 18 may also be coupled to a fluid source for flushing the outer shaft 20, injecting contrast media during a prosthetic valve implantation procedure, and the like.

Figure 3:
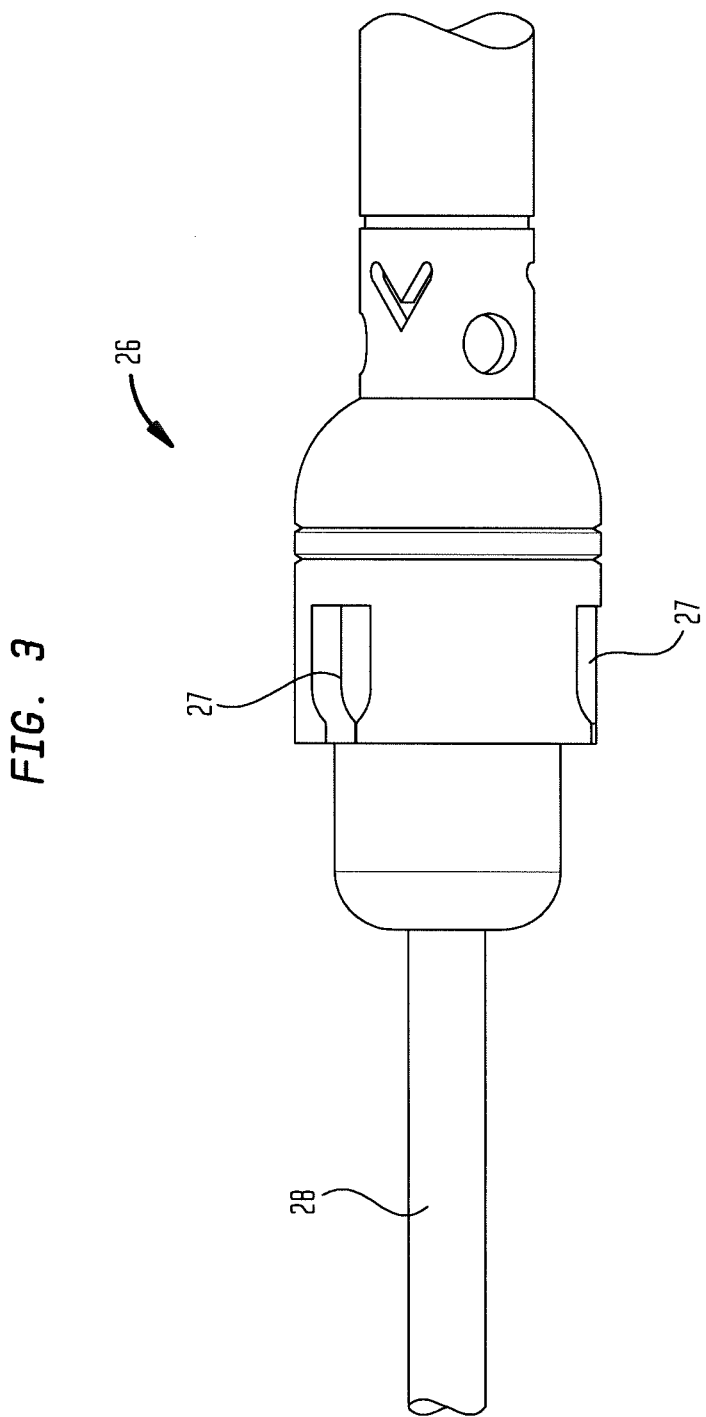
FIG. 3 is an enlarged side view of a retaining element of the delivery device shown in FIGS. 1 and 2.

As shown in FIG. 3, the retaining element 26 may include a plurality of recesses 27 located around its periphery. The recesses 27 are spaced apart from one another and each is sized and shaped to receive a tab or retainer on one end of the prosthetic heart valve to maintain the prosthetic heart valve in assembled relationship with the delivery device 10, to minimize longitudinal movement of the prosthetic heart valve relative to the delivery device during unsheathing and resheathing procedures, to help prevent rotation of the prosthetic heart valve relative to the delivery device as the delivery device is advanced to the target site and during deployment, and to maintain the alignment of the stent cells and prevent them from becoming tangled.

Figure 4:
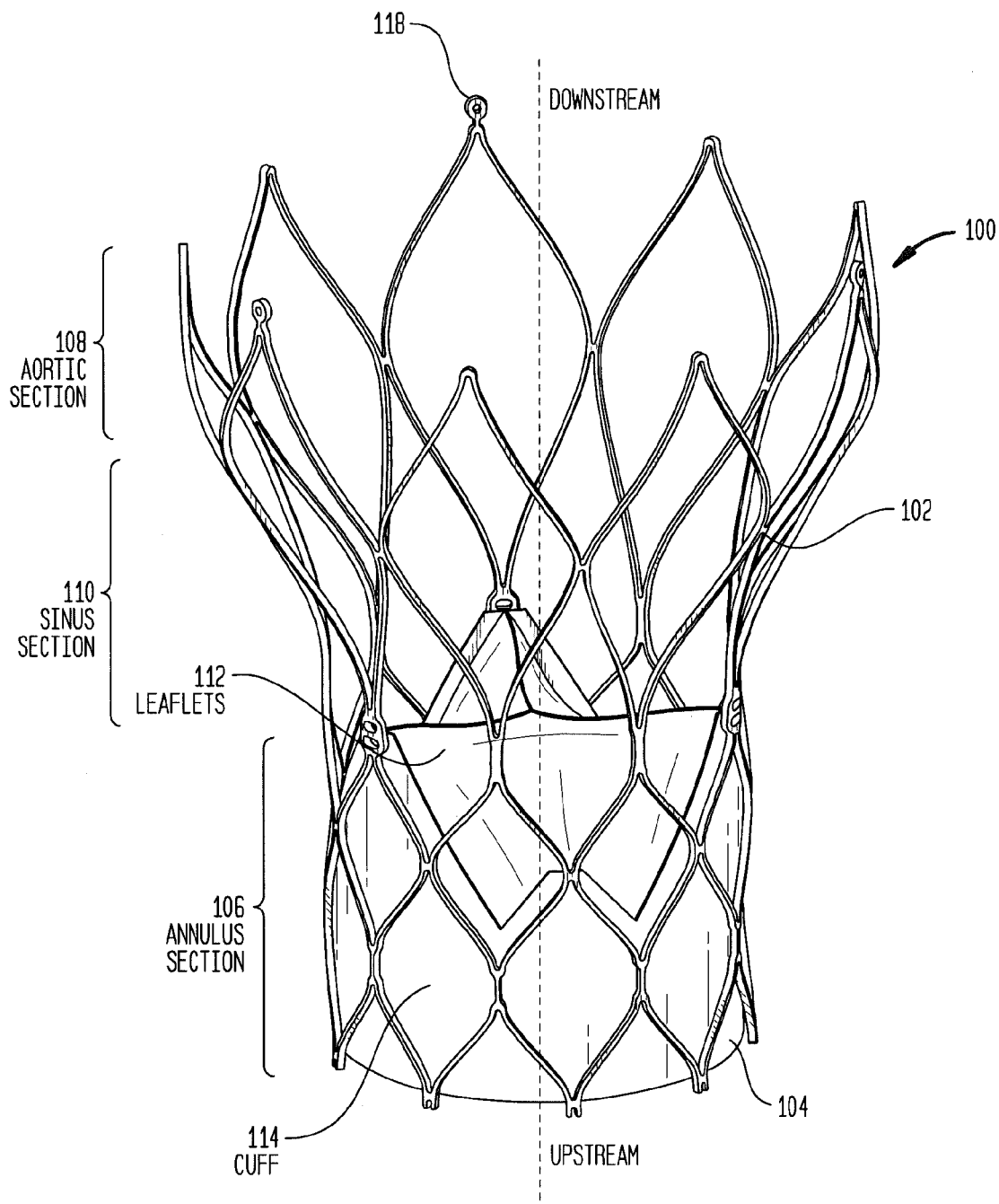
FIG. 4 is a perspective view of a self-expanding prosthetic heart valve.

FIG. 4 shows a conventional bioprosthetic valve 100 designed to replace a native aortic valve. The valve 100 has a collapsed condition and an expanded condition and may be formed from a collapsible framework or stent 102, with a valve assembly 104 internally connected to the stent. The stent 102 may be formed from any suitable biocompatible material, such as nitinol or any other suitable elastic or shape memory material, and may include an annulus section 106, an aortic section 108, and a sinus section 110 located between the annulus section and the aortic section. The aortic section 108 may have a larger cross-section than the annulus section 106. The valve assembly 104 conventionally includes a plurality of leaflets 112 and a cuff 114 attached to the stent 102. The leaflets 112 and the cuff 114 may be formed from a biocompatible polymer, from natural tissue such as bovine or porcine pericardial tissue, or from other appropriate biocompatible materials. The valve assembly 104 is preferably connected to the stent 102 generally within the annulus section 106. The valve 100 may include a plurality of tabs or retainers 118 at spaced positions around one or both ends of the stent 102 for engagement with the retaining elements 26 of the delivery device 10 as described above. The retainers 118 may also be utilized to collapse the valve 100 for loading into the delivery device 10, as will be discussed below.

The valve 100 is preferably stored in its expanded or open condition as the bioprosthetic valve assembly 104 may be compromised by storage in a collapsed condition for extended periods of time. As such, it is necessary to crimp the valve 100 into a collapsed condition of reduced cross-section for loading into the delivery device 10 at the latest possible time prior to the surgical implantation procedure. In order to effectively limit the time period the valve 100 is collapsed, the crimping process is preferably conducted in the operating arena by the surgeon, interventional cardiologist or surgical assistant using a specialized assembly.

Figure 5:
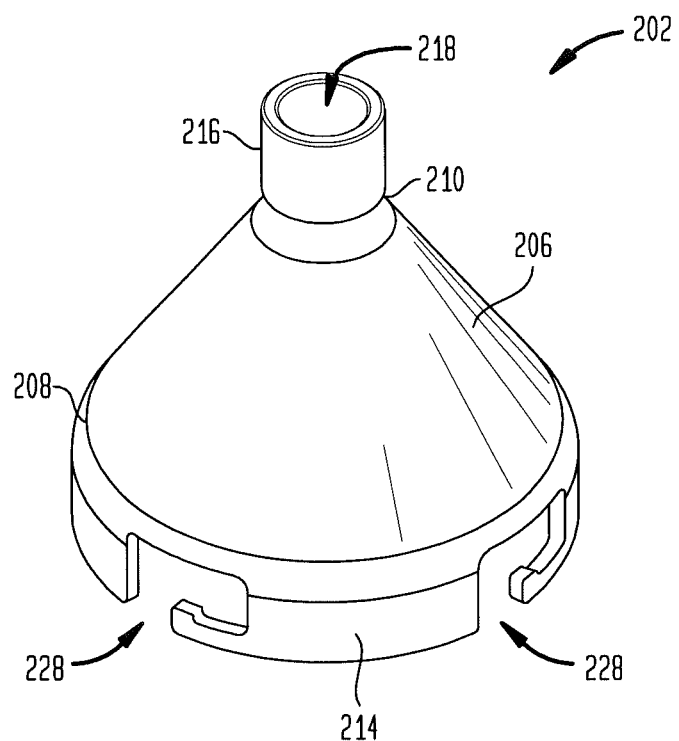
FIG. 5 is a perspective view of a compression member in accordance with an embodiment of the present invention.

FIGS. 5-6 illustrate a loading assembly 200 according to one embodiment of the present invention, the loading assembly generally including a compression member 202 and a support member 204 adapted to be coupled to one another. The compression member 202 includes a funnel 206 having a substantially frusto-conical shape with a large diameter at a first end 208 and a smaller diameter at a second end 210. The diameter of the funnel 206 may decrease uniformly from the first end 208 to the second end 210 to compress the valve 100 as it is advanced through the compression member 202. The compression member 202 is preferably made of a substantially rigid material, and may be wholly or partly made of a transparent plastic, such as polycarbonate or acrylic, to allow viewing of the valve 100 during loading.

The compression member 202 may further include an annular rim 214 extending from the first end 208 of the funnel 206 for joining the compression member to the support member 204 as described below. The rim 214 may include a plurality of slots 228 disposed around its outer periphery. While the drawings show slots 228 that are substantially P-shaped, the slots may have any other shapes suitable for securely holding the compression member 202 to the support member 204. The rim 214 may include four such slots 228, or more or less than four. Regardless of the number or slots 228, adjacent slots are preferably spaced equidistantly from each other.

The compression member 202 also may include a tubular extension 216 projecting from the second end 210 of the funnel 206. The tubular extension 216 has an opening 218 therethrough in communication with the interior of funnel 206. The opening 218 is sized and shaped to receive the distal sheath 30 of the delivery device 10 therein. The cross-section of the tubular extension 216 is preferably substantially circular, but may be oblong, oval, elliptical, or polygonal.

With reference to FIGS. 6A, 6B, 6C and 9, the support member 204 is preferably made in whole or in part of a substantially rigid material, and includes a body 219 having a substantially flat or planar bottom support surface 220 and a top end 221. Body 219 has an outer wall 232 and a generally cylindrical bore 230 extending therethrough. Bore 230 is sized and shaped to receive at least a portion of the tip 32 of the delivery device 10 therein. A recess 226 extends downwardly from the top end 221 of the body 219 concentrically with bore 230 so as to define an annular ridge 244 at a spaced distance from the top end. Ridge 244 may have a chamfered surface 246 at its intersection with bore 230. Alternatively, a chamfered surface 246 may not be included. Recess 226 has a diameter and a depth defined by ridge 244 sufficient to receive at least a portion of the annulus section 106 of the stent 102 in an expanded condition.

Figure 6A:
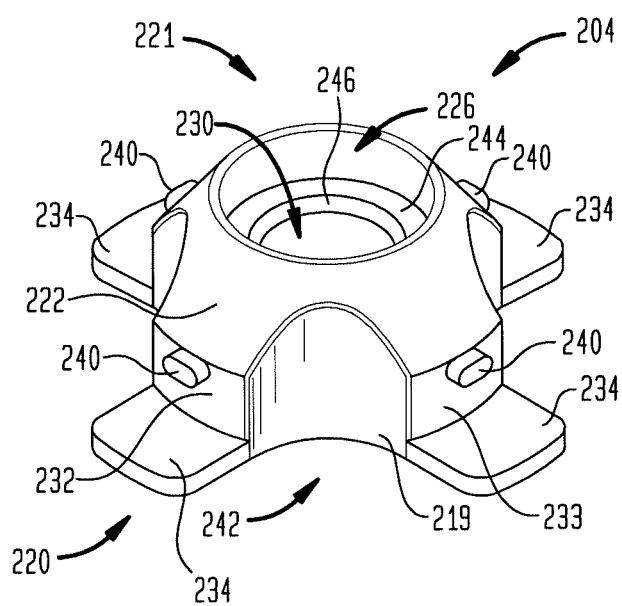
FIG. 6A is a perspective view of a support member in accordance with an embodiment of the present invention.
Figure 6B:
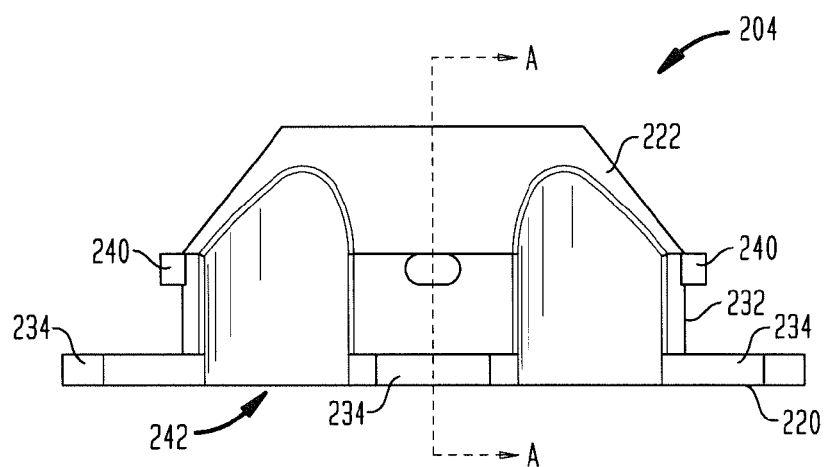
FIG. 6B is a side elevational view of the support member of FIG. 6A.
Figure 6C:
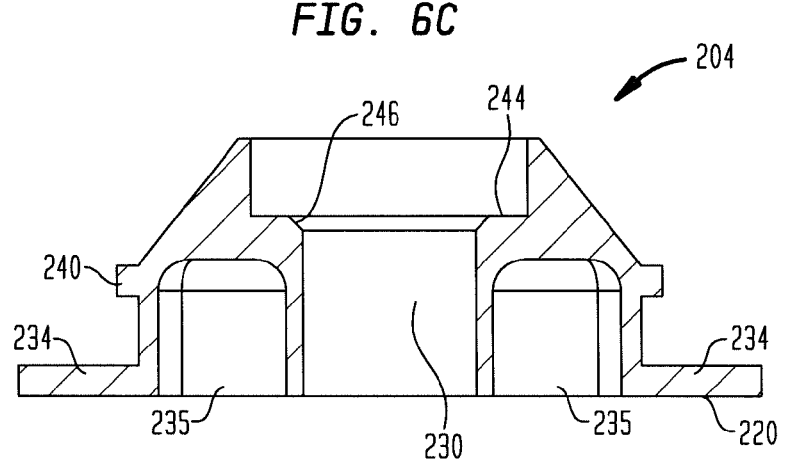
FIG. 6C is a cross-sectional view of the support member of FIG. 6A, taken along section line A-A of FIG. 6B.

The outer wall 232 of body 219 does not extend continuously around the body, but rather is interrupted by a plurality of inwardly curved indentations 242 which divide the outer wall into a plurality of wall segments 233, only two of which are shown in FIG. 6A. Although FIG. 6A depicts a support member 204 having four indentations 242 evenly spaced around the periphery of body 219, it is contemplated that the support member may be provided with more or less than four such indentations. Indentations 242 facilitate the grasping of support member 204. Between indentations 242, that is, in the space between outer wall segments 233 and bore 230, body 219 may include a plurality of recesses 235 extending inwardly from the bottom support surface 220. Recesses 235 reduce the mass of body 219 and facilitate the manufacturing process by eliminating excessively thick portions of the body.

The outer wall segments 233 of body 219 do not extend all the way to the top end 221 of the body, but rather terminate at their top ends at a continuous wall 222 oriented at an oblique angle to the outer wall 232. At their bottom ends, outer wall segments 233 each include a radially projecting supporting plate 234, the bottom surfaces of which are substantially coplanar with the bottom support surface 220 of body 219. At least one pin 240 may protrude radially outward from each outer wall segment 233. Pins 240 are preferably spaced a sufficient distance from supporting plates 234 and sized and shaped to be received in the slots 228 of the compression member 202 to join the compression member and the supporting member 204 together. When joined together, the compression member 202 and the supporting member 204 collectively define a partial loading assembly 201.

Figure 7:
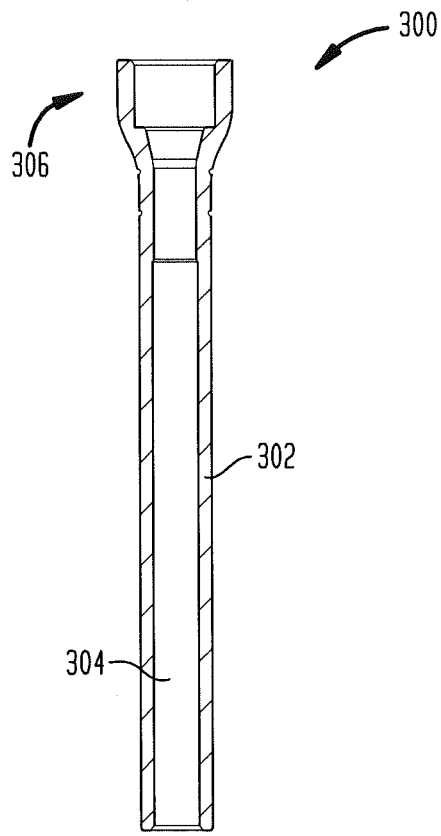
FIG. 7 is a longitudinal cross-sectional view of a constricting member in accordance with an embodiment of the present invention.
Figure 8:
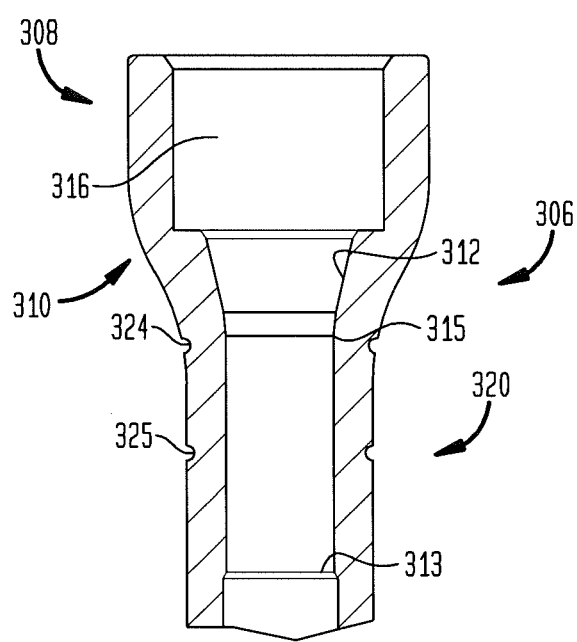
FIG. 8 is an enlarged longitudinal cross-sectional view of an end section of the constricting member of FIG. 7.

FIGS. 7 and 8 illustrate a constricting member 300 designed to minimize the flaring of the distal end 21 of the distal sheath 30 during loading of a prosthetic heart valve into the compartment 23 of delivery device 10. The constricting member 300 may be wholly or partly made of a transparent plastic, such as polycarbonate or acrylic, to allow viewing of the delivery device 10 during loading and includes a tubular member 302 having a central lumen 304 sized and shaped to slidingly receive at least the distal sheath 30 of the delivery device 10.

As seen in FIG. 8, at one end 306, the constricting member 300 may have an enlarged head 308 with a counterbore 316 formed therein. The counterbore 316 may have a diameter that is larger than the diameter of lumen 304, and in particular, may be sized and shaped to receive the tubular extension 216 of the compression member 202. Preferably, the diameter of counterbore 316 is only slightly larger than the outer diameter of the tubular extension 216 so as to create a friction fit therebetween.

Between the tubular member 302 and the enlarged head 308, constricting member 300 may have a tapered portion 310. In particular, tapered portion 310 may have an inner surface 312 which tapers from a larger diameter at its end adjacent the counterbore 316 to a smaller diameter at its other end to help compress valve 100 further during loading into delivery device 10.

The constricting member 300 may further include a transition portion 320 disposed between the tapered portion 310 and the tubular member 302. The transition portion 320 may have a substantially constant inner diameter sized and shaped to receive at least the distal sheath 30 of the delivery device 10. The inner diameter of the transition portion 320 may be slightly smaller than the diameter of lumen 304 and slightly larger than the outer diameter of the distal sheath 30 in order to substantially prevent or minimize the flaring of the distal end 21 of the distal sheath 30 while the valve 100 is loaded in the delivery device 10, as discussed in detail below. The larger diameter of the lumen 304 allows a user to easily slide the constricting member 300 over the distal sheath 30 of the delivery device 10. In a variant hereof, the transition portion 320 may have an inner diameter which tapers downwardly from a slightly larger diameter at an end 313 thereof to a slightly smaller diameter at an end 315 thereof to accommodate small variations in the outer diameter of the distal sheath 30.

An annular groove or other indicator line 324 may extend partly or entirely around the outer periphery of the tubular member 302 at the junction between the tapered portion 310 and the transition portion 320. Another annular groove or indicator line 325 may extend partly or entirely around the outer periphery of the tubular member 302 at a spaced distance from the first line 324. Lines 324 and 325 mark the area in which the user should place the distal end 21 of the distal sheath 30 during the loading procedure. As discussed in detail below, using the constricting member 300 to help load the valve 100 into the delivery device 10 reduces the loading forces (i.e., the forces required to load the valve into the delivery device) and reduces flaring of the distal end 21 of the distal sheath 30.

Figure 9:
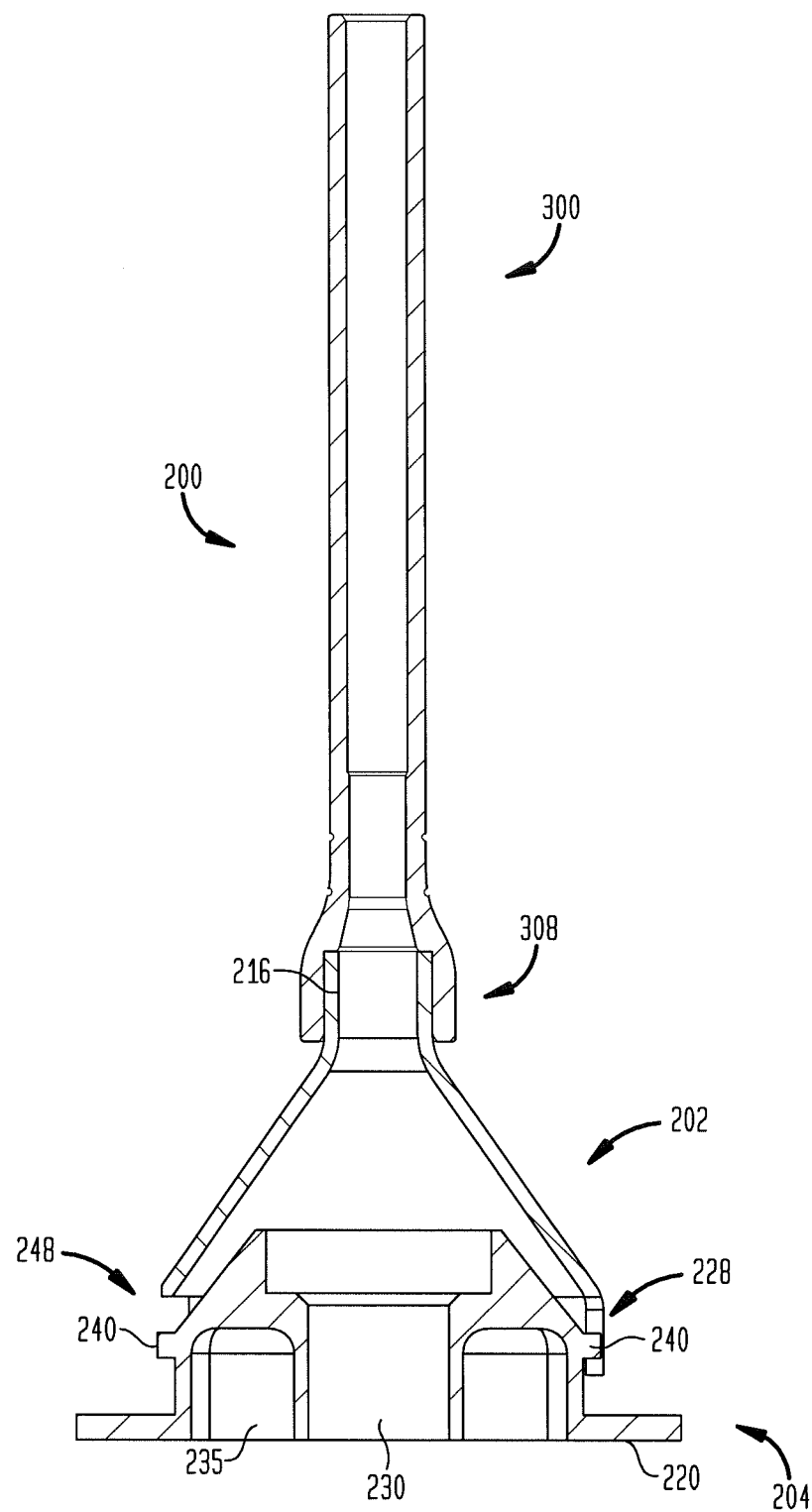
FIG. 9 is a longitudinal cross-sectional view of a loading assembly in accordance with an embodiment of the present invention, including the compression member of FIG. 5, the support member of FIG. 6A, and the constricting member of FIG. 7.

FIG. 9 shows an assembled loading assembly 200 including the compression member 202 of FIG. 5, the support member 204 of FIG. 6 and the constricting member 300 of FIG. 7. As seen in FIG. 9, the constricting member 300 is connected by its enlarged head 308 to the tubular extension 216 of the compression member 202, and the compression member 202 is locked to the support member 204. To lock the compression member 202 to the support member 204, the pins 240 of the support member are inserted into the slots 228 of the compression member, and the compression member is turned relative to the support member to slide the pins toward the closed ends of the slots. Hence, the pins 240 and the slots 228 together form a locking mechanism 248. Rather than the engagement of the pins 240 in the slots 228, it is contemplated that any other known locking mechanisms may be employed to securely lock the compression member 202 to the support member 204.

Figure 10:
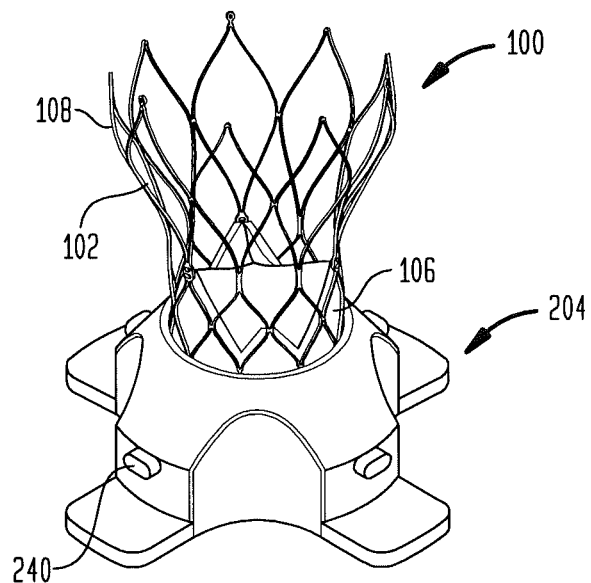
FIGS. 10-19 illustrate the steps of a method for loading a prosthetic heart valve into a delivery device using the loading assembly of FIG. 9.
Figure 11:
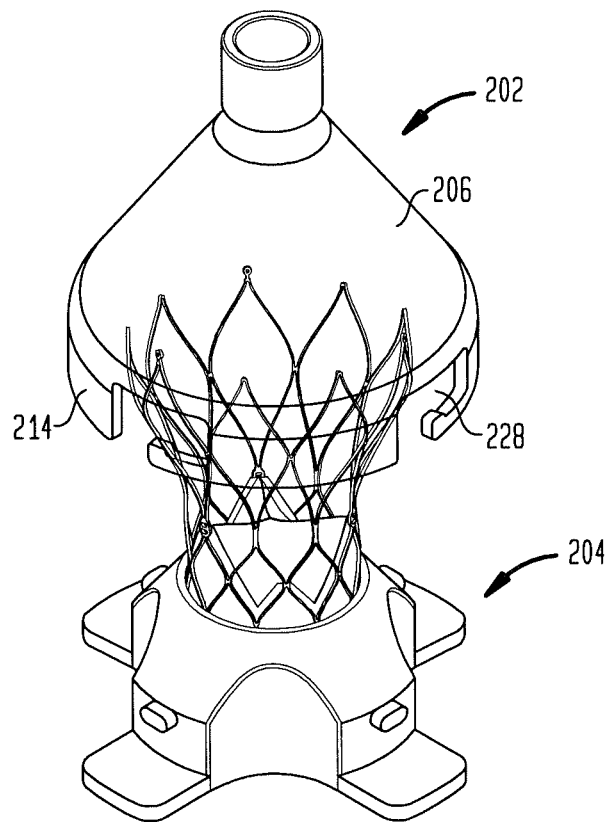
Figure 12:
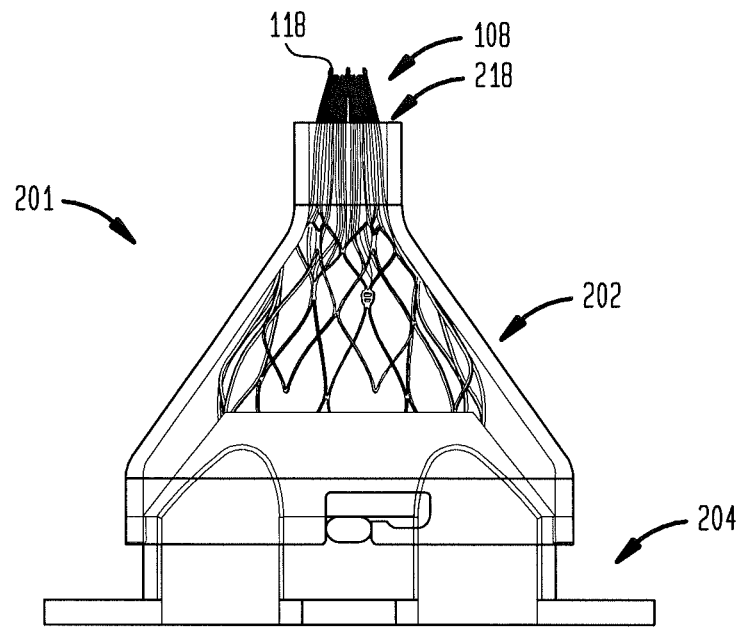

As seen in FIGS. 10-19, the loading assembly 200 may be used to load the collapsible prosthetic heart valve 100 into a delivery device 10. As shown in FIG. 10, with the supporting member 204 on a flat surface, at least a portion of the annulus section 106 of the stent 102 may be placed within the recess 226 of the support member until the end of the stent contacts ridge 244. The compression member 202 may then be placed over the aortic section 108 of the stent 102 so that the aortic section of the stent is positioned within the funnel 206, as depicted in FIG. 11. As shown in FIG. 12, the compression member 202 and the support member 204 may then be pushed together, the tapered walls of the funnel 206 gradually compressing the valve 100 until a portion of the aortic section 108 of the stent 102 is forced into and through the opening 218 of the compression member. When a portion of the aortic section 108 of the stent 102 passes through the opening 218 of the compression member 202, the retainers 118 of the stent will protrude through the opening 218 and will be positioned closely adjacent to one another. At this point, the pins 240 of the support member 204 will be positioned within the slots 228 of the compression member 202, and the members may be locked together by rotating the support member relative to the compression member, such that the pins 240 of the support member slide toward the closed ends of the slots 228 of the compression member.

Figure 14A:
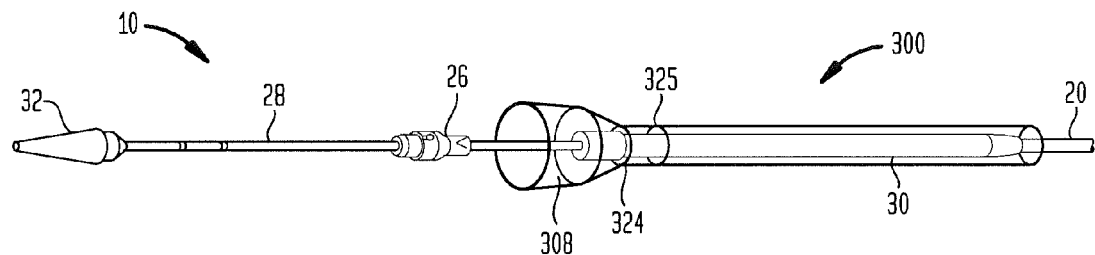

As seen in FIG. 14A, with the distal sheath 30 in a proximal or open position, the constricting member 300 may be placed over the delivery device 10 with the enlarged head 308 positioned closer to the tip 32 than to the hub or handle of the delivery device, and with the distal end 21 of the distal sheath 30 longitudinally positioned between indicator lines 324 and 325 of the constricting member. It will be appreciated that the constricting member 300 also may be placed over the delivery device 10 with the distal sheath 30 in the distalmost or closed position, and that the distal sheath subsequently may be moved to the proximal or open position.

Figure 14B:
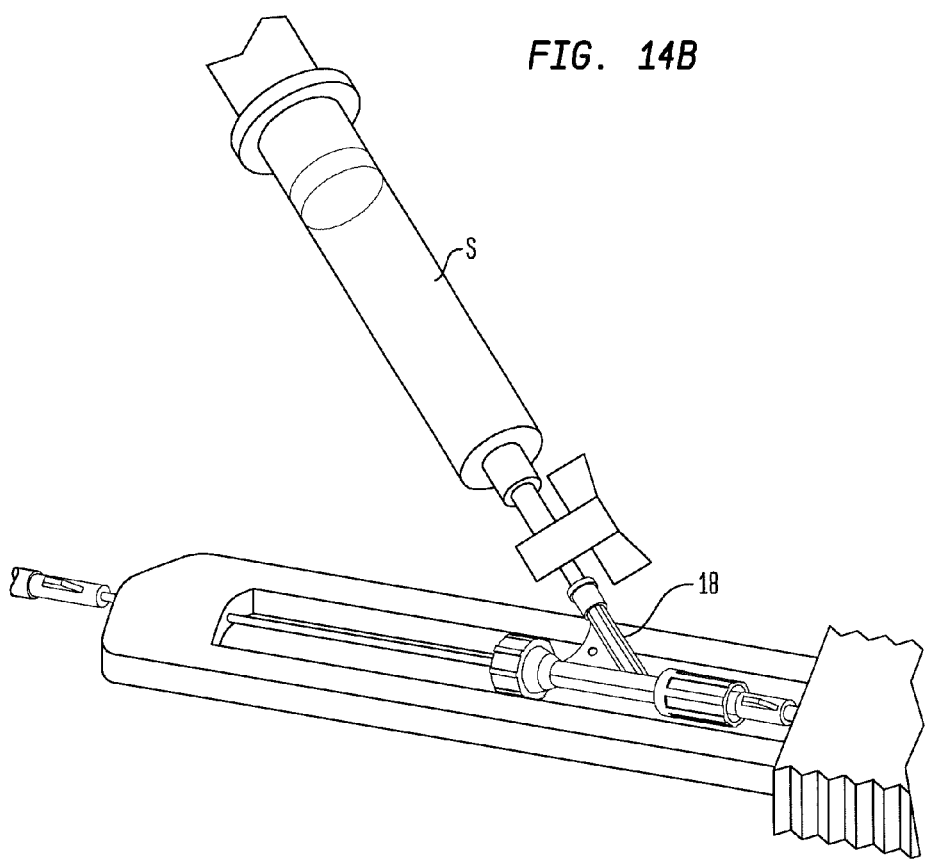

Before loading the valve 100 into the delivery device 10, it is preferable to subject the delivery device to a deairing process. In that regard, with the constricting member 300 assembled over the distal sheath 30 and the distal sheath in an open position, a syringe S may be connected to the Y-connector 18 of the delivery device 10, as shown in FIG. 14B. The syringe may be used to inject a sterile liquid, such as saline, into the proximal end of the delivery device and out through the open compartment 23, thereby flushing the air from the device. During this flushing step, the distal end of the delivery device may be tapped multiple times to facilitate the air removal.

Figure 13:
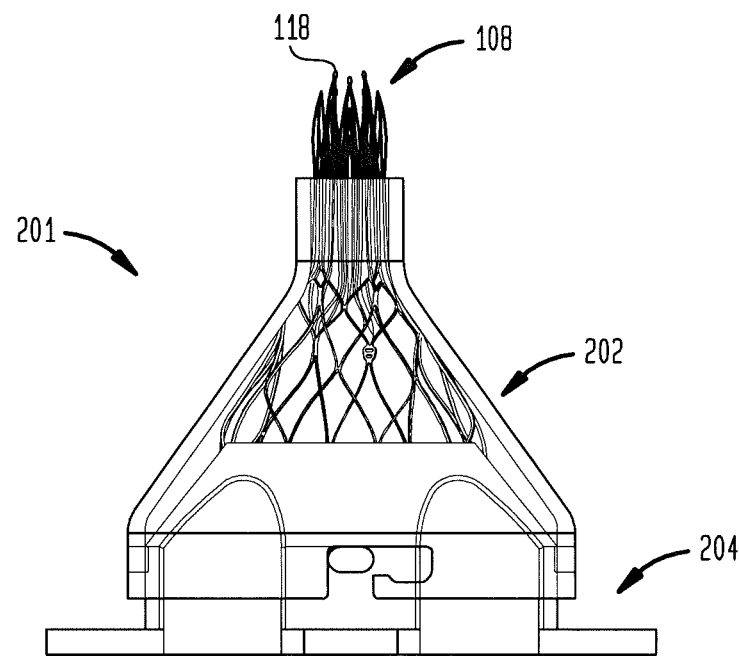
Figure 15:
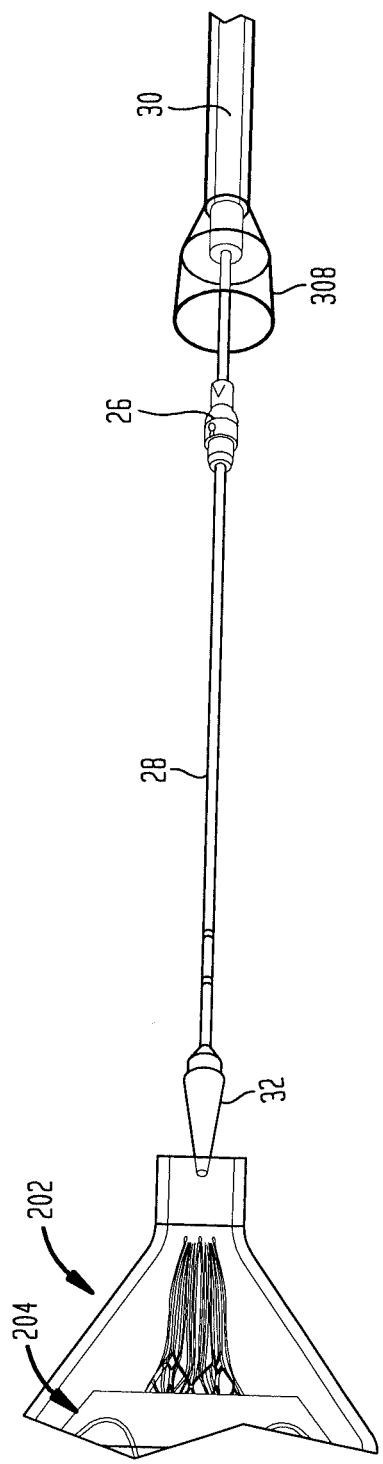
Figure 16:
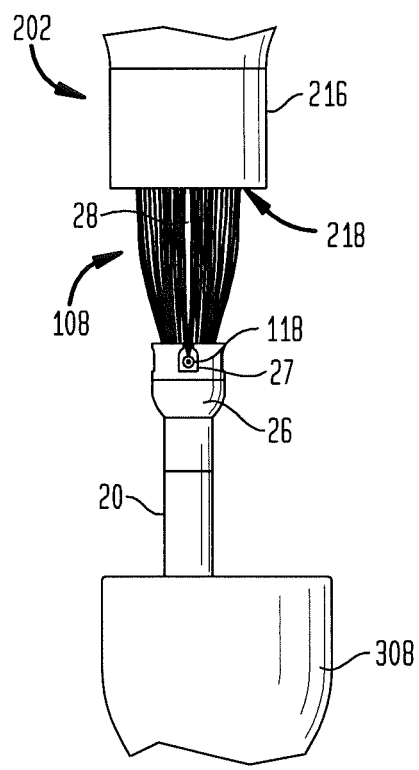

Once flushing of the delivery device 10 has been completed, the tip 32 and the support shaft 28 of the delivery device 10 may be inserted into the end of the collapsed valve 100 protruding from the opening 218 of the compression member 202. To accomplish this, the compression member 202 and the support member 204 may be squeezed closer together. (The dimension of the slots 228 in the longitudinal direction, i.e., the height of the slots, is greater than the dimension of the pins 240 in the longitudinal direction, i.e., the height of the pins. Therefore, even though the compression member 202 and the support member 204 are assembled together, they still may move further toward one another.) As the compression member 202 and the support member 204 move closer together, a greater portion of the stent 102 is forced out through opening 218, causing the retainers 118 to begin to separate from one another, as illustrated in FIG. 13. The tip 32 and support shaft 28 of the delivery device 10 may then be inserted between the retainers 118 and into the end of the collapsed valve 100, as shown in FIG. 15. The partial loading assembly 201 then may be advanced along the support shaft 28 until the retainers 118 of the stent 102 are positioned over the retaining element 26 of the delivery device 10. The partial loading assembly 201 may be twisted as needed to align the retainers 118 with the recesses 27 in the retaining element 26. Positioning the retainers 118 within the recesses 27 of the retaining element 26 attaches the stent 102 to the delivery device 10, as seen in FIG. 16. With the stent 102 attached to the retaining element 26, the constricting member 300 and the distal sheath 30 may be slid together toward the partial loading assembly 201 (or the inner tube 16 may be moved proximally relative to the constricting member 300 and the distal sheath 30) to about the position shown in FIG. 17, in which the distal sheath covers the retainers 118 of the stent, at the same time maintaining the distal end 21 of the distal sheath between indicator lines 324 and 325. The tapered inner surface 312 of the enlarged head 308 facilitates the compression of the stent 102 as it moves into the constricting member 300. When the constricting member 300 and the partial loading assembly 201 are close together, they may be joined to one another by assembly of the enlarged head 308 of the constricting member 300 to the tubular extension 216 of the compression member 202.

Figure 17:
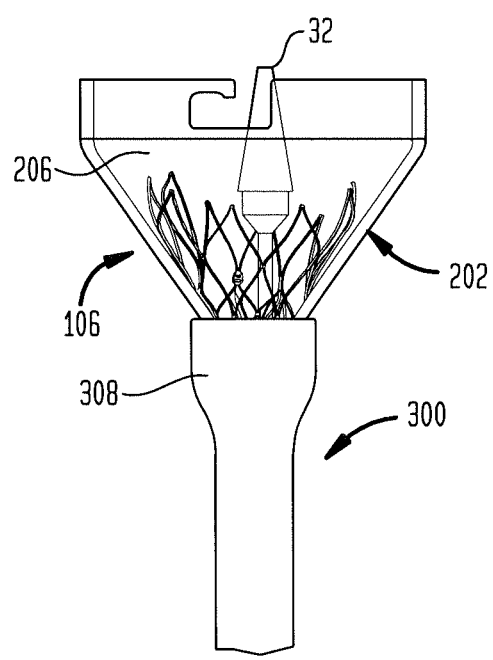

In order to deair the valve 100, a sterile liquid, such as saline, may be dispensed into the compression member 202 through its first open end 208. To do so, the support member 204 may be disassembled from the compression member 202 by first rotating the support member relative to the compression member, such that the pins 240 of the support member slide toward the open ends of the slots 228 of the compression member. This action unlocks the members from one another. The support member 204 may then be moved away from the compression member 202 to disassemble the partial loading assembly 201. With the first open end 208 of the funnel 206 facing up, the sterile liquid may be dispensed into the compression member 202 through the first open end. The sterile liquid may be dispensed into the compression member 202, such as through a syringe or a sterile container, until the funnel 206 is substantially filled, as shown in FIG. 17. The syringe may need to be refilled several times during the injection process in order to fill the funnel 206 with the sterile liquid.

Any air bubbles in the sterile liquid within the funnel 206 may then be removed. It is important that little or no air be released into the human body during deployment and/or resheathing of the valve within the human heart, as the air may block vascular flow and cause tissue damage. For this reason, it is important to remove air bubbles from the delivery device 10 and the valve 100 before introducing them into the body. Testing has shown that, if the methods and assemblies described in this application are employed, minimal air will be released into the patient's bloodstream during valve deployment and resheathing.

Figure 18:
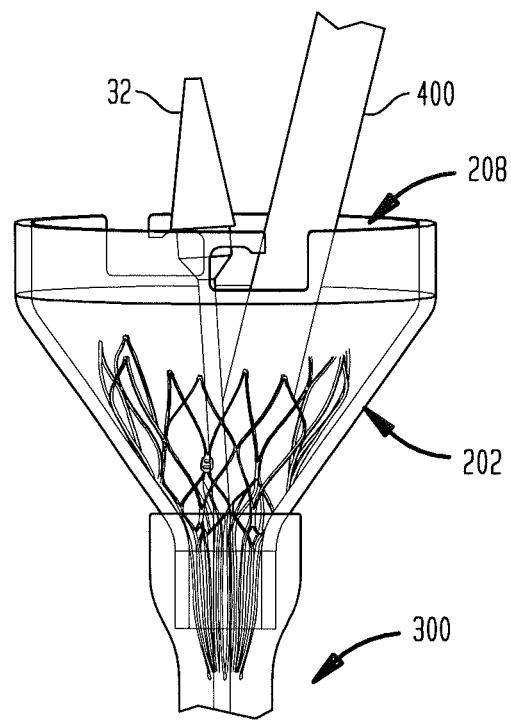

Air bubbles formed in the sterile liquid near the space between the leaflets 112 and the cuff 114 of the valve 100 may be removed by using a tube or rod 400 or any other suitable atraumatic probe. The tube 400 is commonly known in the art as a "leaflet tester" and may be formed of a substantially soft material, such as a soft polymer. In order to remove the air bubbles from the sterile liquid, the tube 400 may be placed into the sterile liquid contained in the funnel 206 of the compression member 202 and used to probe areas of potential air entrapment, including gently agitating the liquid, as shown in FIG. 18. A syringe may be used to remove the air bubbles from the space near the retaining element 26 of the delivery device 10. To do so, the syringe may be inserted into the space near the retaining element 26, and the sterile liquid near the retaining element 26 may be gently agitated with the syringe. After the air bubbles have been removed, the valve 100 may be pulled into the distal sheath 30 until the valve is completely covered, as seen FIG. 19. The constricting member 300 and the compression member 202 may then be removed from the delivery device 10. The inner tube 16 of the delivery device 10 may then be flushed with any suitable sterile liquid using, for example, a syringe. To flush the inner tube 16, a syringe may be connected to the hemostatic valve near the hub 14 of the delivery device 10, and then sterile liquid may be injected into the inner tube using the syringe.

In an alternate method of loading the valve 100 into the delivery device 10 and preparing same for use in a patient, the air bubbles may be removed from the distal sheath by submerging the distal sheath, the compression member 202, and the constricting member 300 in a container holding sterile liquid, such as saline. Additional sterile liquid may be injected into the delivery device 10 through the Y-connector 18 using a syringe, as discussed above. The distal sheath 30 of the delivery device 10 may then be shaken and gently tapped against a hard surface to remove air bubbles from the valve 100. The valve 100 may then pulled into the distal sheath 30, as discussed above.

In view of the tight fit between the collapsed valve 100 and the distal sheath 30, significant friction forces must be overcome in order to move the distal sheath 30 completely over the valve 100. To facilitate this procedure, the stent 102 may be substantially cooled, which, depending on the materials forming the stent, may enable the stent to more easily deform. Thus, once more than about one-half of the length of the stent 102 has been covered by the distal sheath 30, a cold liquid, such as saline solution, may be applied to the stent through the compression member 202 and the constricting member 300. This may be accomplished by removing the support member 204 from the compression member 202 and holding the remainder of the assembly in a substantially vertical orientation with the first end 208 of the funnel 206 facing upwardly. The cold liquid may then be introduced into the compression member 202 using any suitable apparatus. It will, of course, be appreciated that the cold liquid may thus serve two purposes—it may cool the stent 102, and it may serve as the deairing liquid in the deairing procedure described above.

Figure 19:
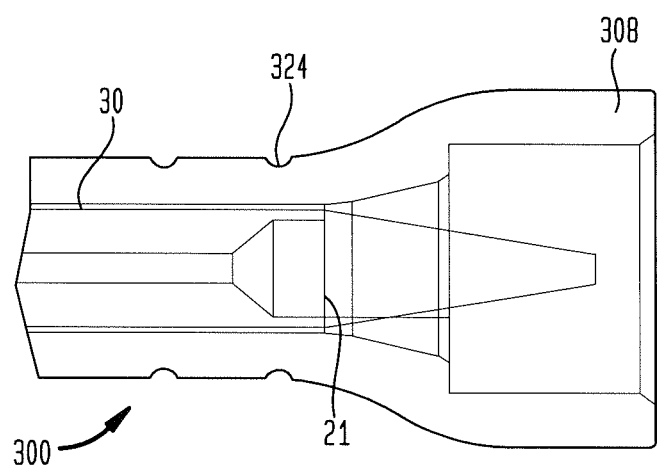

In order for the cooling of the stent 102 to be effective in making it easier for the stent to be completely covered by the distal sheath 30 of the delivery device 10, the stent should be cooled to a temperature below the transition temperature of the material forming the stent. The "transition temperature" of a material is the temperature at which the material changes from one crystal state to another. For the nitinol stents that may be employed in the present invention, a saline solution at about 0° C. may be used. When cooled below its transition temperature, the stent 102 becomes plastic, enabling it to deform much more readily under the forces exerted by the movement of the distal sheath 30 thereover. Accordingly, after the stent 102 has been cooled below the transition temperature, the user may completely cover the stent 102 with the distal sheath 30 of the delivery device 10, as illustrated in FIG. 19.

The distal sheath 30 of the delivery device 10 should be non-traumatic. To accomplish this, the distal sheath 30 may be made of soft polymeric material. However, while the valve 100 is loaded into the delivery device 10, the distal end 21 of the distal sheath 30 may slightly expand or flare due to the pressure exerted by the self-expanding stent 102. Since the distal sheath 30 is typically formed from a soft polymer, the distal end 21 of the distal sheath may not return to its original shape once the distal sheath completely covers the valve 100. It is nonetheless important to maintain the original cross-sectional profile of the distal end 21 of the distal sheath 30, because doing so makes the distal sheath more atraumatic and reduces the loading forces required to load the valve 100 into the delivery device 10. In order to maintain the original circular profile of the distal end 21 of the distal sheath 30, the loading assembly 200 preferably includes the constricting member 300 described above.

Figure 20:
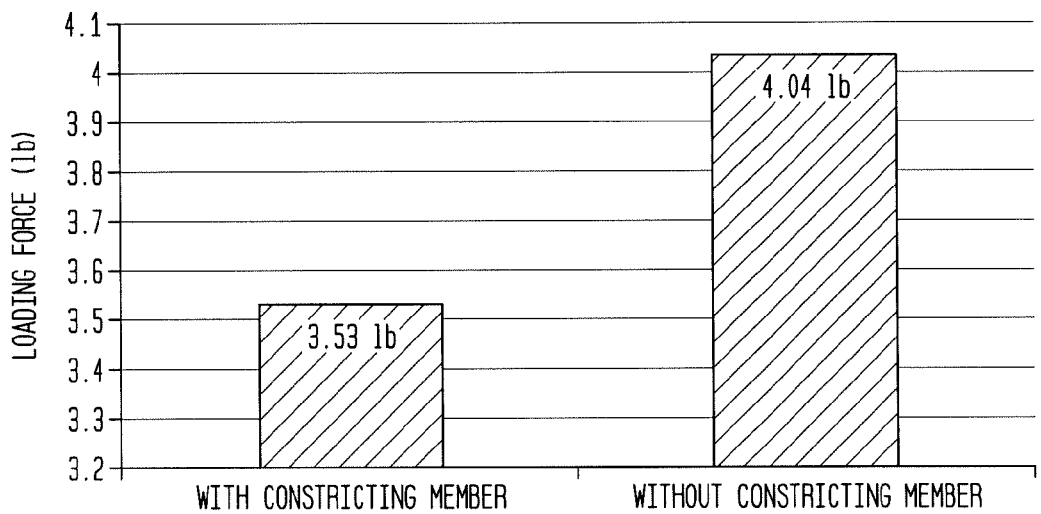
FIG. 20 is a table including test data of a study analyzing the use of the constricting member of FIG. 7 while loading the valve of FIG. 4 into the delivery device of FIG. 1 and its effect on the forces required for loading the valve.

FIG. 20 is a table with test data demonstrating the advantages of loading the valve 100 into the delivery device 10 using a constricting member 300. This table shows that loading the valve 100 into the delivery device 10 using the constricting member 300 reduces the loading forces (on average) by approximately 13% in comparison to a loading procedure in which a constricting member is not used. The term "loading forces" refers to the forces required to slide the distal sheath 30 of the delivery device 10 over the entire valve 100. As discussed above, the valve 100 is partially compressed by the partial loading assembly 201, and must be compressed further as the distal sheath 30 is slid thereover. The term "loading forces" therefore encompasses the forces required to slide the distal sheath over the valve, thereby further compressing the valve, until the distal sheath is in the closed condition with the valve fully covered.

Figure 21:
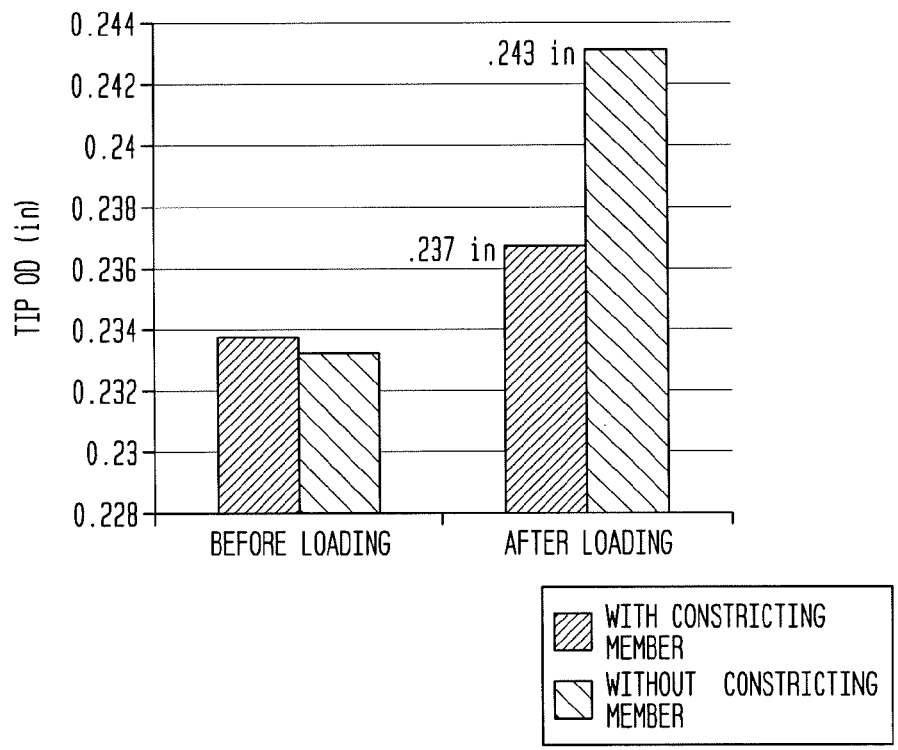
FIG. 21 is a table including test data of a study analyzing the use of the constricting member of FIG. 7 while loading the valve of FIG. 4 into the delivery device of FIG. 1 and its effect the distal end of the distal sheath of the delivery device of FIG. 1.

FIG. 21 is another table with test data demonstrating the advantages of loading the valve 100 into the delivery device 10 using the constricting member 300. This table shows that loading the valve 100 into the delivery device 10 using the constricting member 300 reduces flaring of the distal end or tip 21 of the distal sheath 30 (on average) by about 67% in comparison to a loading procedure in which a constricting member is not used.

Figure 22:
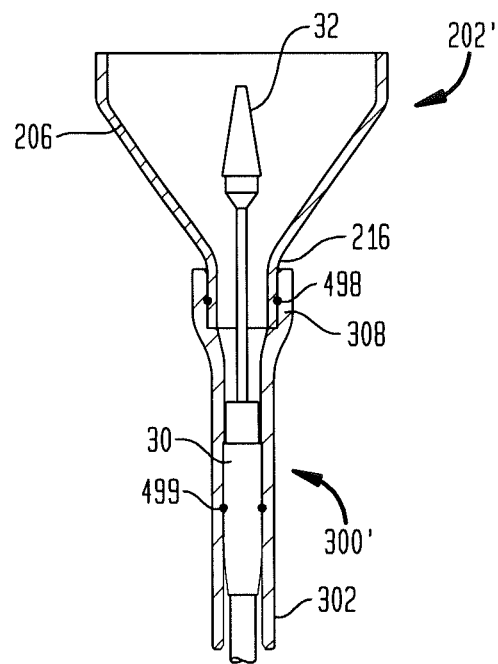
FIG. 22 is a cross-sectional side view of a loading assembly in accordance with an alternate embodiment of the present invention.

FIG. 22 shows a compression member 202' and a constricting member 300' which may include one or more seals 498 and 499 for preventing any sterile liquid contained in the compression member from leaking while loading the valve 100 into the delivery device 10 and preparing it for use. The first seal 498 may be formed from an impermeable material and may be disposed between the inner surface of the enlarged head 308 of the constricting member 300' and the outer surface of the tubular extension 216 of the compression member 202'. The first seal 498 may be in the form of an O-ring resting in an annular groove on the outer surface of the tubular extension 216 of the compression member 202' or in an annular groove on the inside surface of the enlarged head 308 of the constricting member 300'. The second seal 499 may also be made of an impermeable material, preferably in the form of an O-ring, and may rest in an annular groove formed on the inner surface of the tubular member 302 of the constricting member 300'. When the constricting member 300' is placed over the distal sheath 30 of the delivery device 10, the second seal 499 is disposed between the inner surface of the constricting member and the outer surface of the distal sheath 30.

Figure 23:
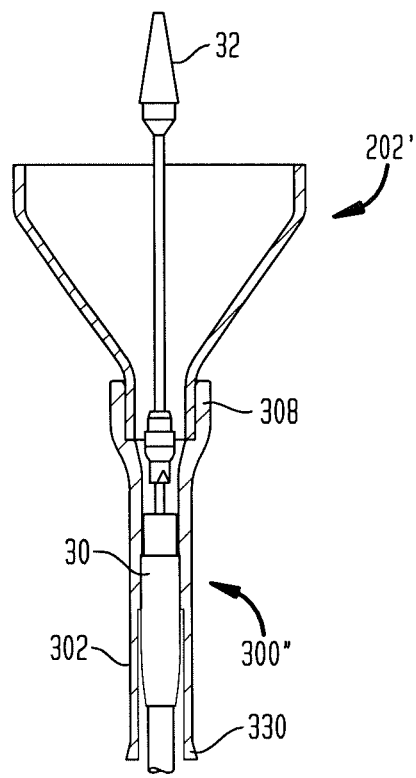
FIG. 23 is a cross-sectional side view of a loading assembly in accordance with a further embodiment of the present invention.

FIG. 23 depicts a constricting member 300'' which may include a portion 330 projecting radially outward at the end opposite the enlarged head 308 for facilitating placement of the constricting member 300'' over the distal sheath 30 of the delivery device 10. The outer diameter of the end portion 330 may be larger than the outer diameter of the rest of the tubular member 302, except for the enlarged head 308. Such larger outer diameter allows a user to easily grab the constricting member 300'' while placing it over the distal sheath 30 of the delivery device 10.

Figure 24:
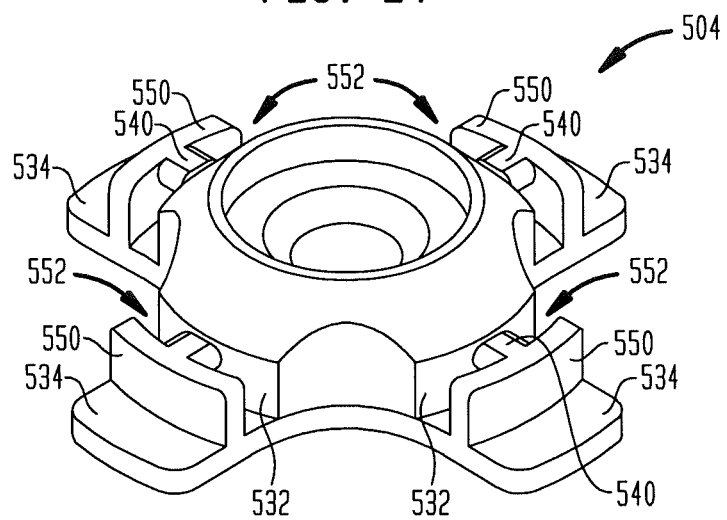
FIG. 24 is a perspective view of a support member in accordance with yet another embodiment of the present invention.

Many variants of the support member, compression member and constricting member are available which will function in substantially the same way as the components of the loading assembly 200 described above. FIG. 24 shows a support member 504 in accordance with an alternate embodiment of the present invention. The structure and operation of this support member 504 is similar to the support member 204 shown in FIGS. 6A-6C. However, unlike support member 204, support member 504 may include an additional wall 550 extending upwardly from one or more supporting plates 534 at a spaced distance from outer wall 532, thereby defining a slot 552 between the outer wall and the additional wall. The slot 552 is sized and shaped to receive at least a portion of the rim 214 of compression member 202. Though the embodiment shown in FIG. 24 includes four supporting plates 534 and four additional walls 550, the support member 504 may include more or fewer such plates and additional walls. Further, each pin 540 of the support member 504 extends inwardly from the additional wall 550 toward a segment of outer wall 532. In the embodiment depicted in FIG. 24, each pin 540 extends inwardly from the center of a top edge of the additional wall 550; however, each pin 540 may extend inwardly from any other locations of the additional wall 550 so long as there is sufficient clearance between the pin and the supporting plate 534 to assemble the compression member 202 to the support member 504. Irrespective of the exact location of each pin 540 on its respective wall 550, each pin is sized and shaped to be received by a slot 228 of the compression member 202.

Figure 25A:
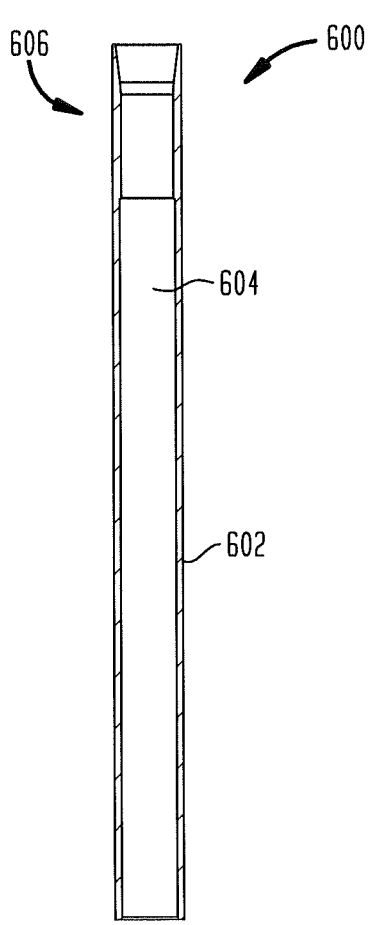
FIG. 25A is a longitudinal cross-sectional view of a constricting member in accordance with another embodiment of the present invention.
Figure 25B:
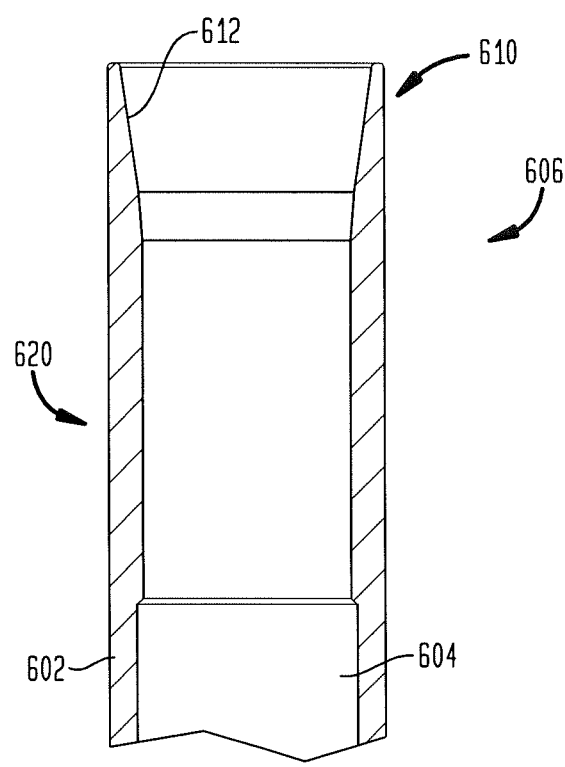
FIG. 25B is an enlarged longitudinal cross-sectional view of an end section of the constricting member of FIG. 25A.

FIGS. 25A and 25B show a constricting member 600 similar to the constricting member 300 depicted in FIG. 7. The constricting member 600 is configured to prevent or minimize the flaring of the distal end 21 of the distal sheath 30 during loading of prosthetic valve 100 into delivery device 10, and may be wholly or partly made of a transparent material, such as polycarbonate or acrylic, to allow viewing of the delivery device during the loading procedure. The constricting member 600 may include a tubular member 602 having a central lumen 604 sized and shaped to slidingly receive at least a portion of the distal sheath 30 of the delivery device 10.

As seen in FIG. 25B, constricting member 600 may have a funnel portion 610 at one end 606 of the tubular member 602. The funnel portion 610 may have an inner surface 612 which tapers from a larger diameter at an end of constricting member 600 to a smaller diameter where the inner surface 612 meets lumen 604 to help compress the valve 100 during loading into delivery device 10. The outer diameter of funnel portion 610, however, is preferably about the same as the outer diameter of tubular member 602, and in particular, is sized and shaped for insertion into the opening 218 of the compression member 202 for assembling the constricting member 600 to the compression member. The constricting member 600 may further include a transition portion 620 disposed between the funnel portion 610 and the tubular member 602. The inner diameter of the transition portion 620 may be slightly smaller than the inner diameter of lumen 604 and slightly larger than the outer diameter of the distal sheath 30 in order to substantially prevent or minimize the flaring of the distal end 21 of the distal sheath 30 while the valve 100 is loaded in the delivery device 10. The larger diameter of the lumen 604 allows a user to easily slide the constricting member 600 over the distal sheath 30 of the delivery device 10.

Figure 26:
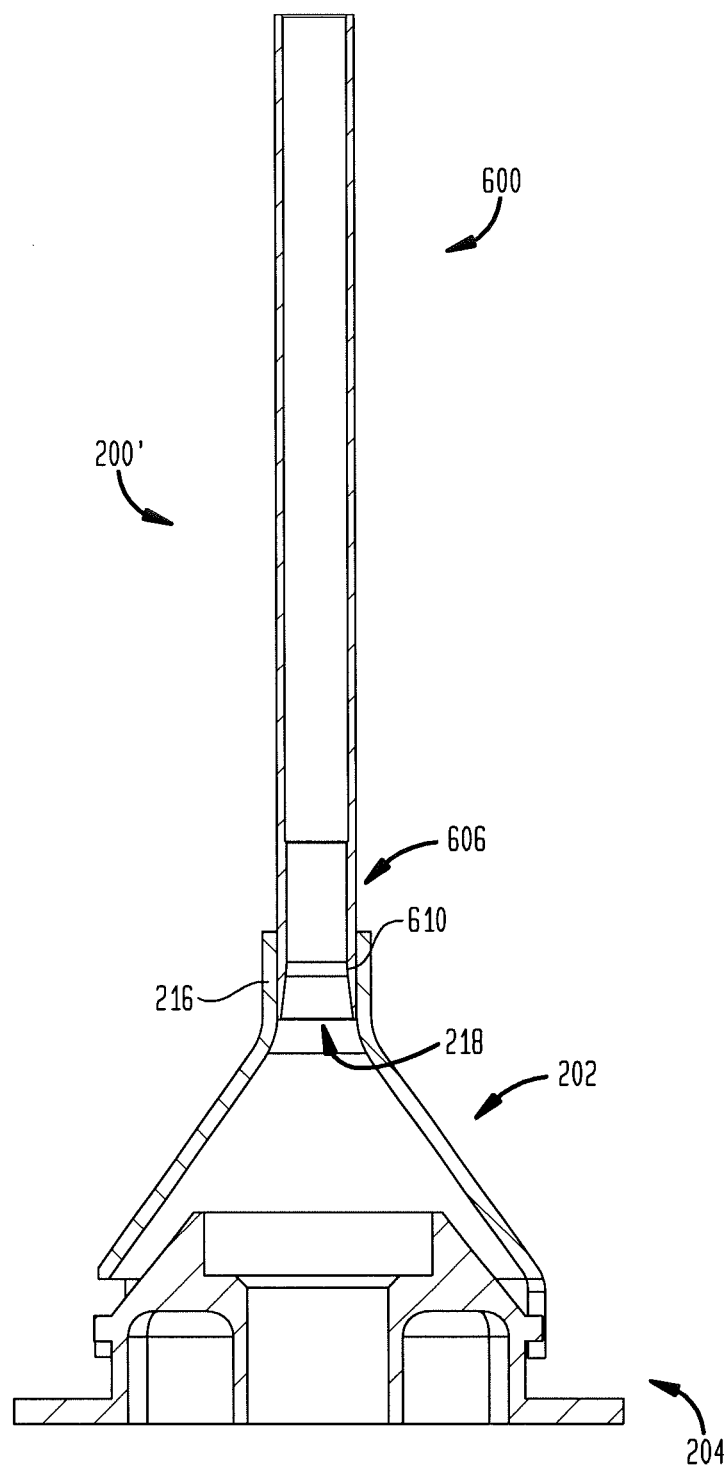
FIG. 26 is a longitudinal cross-sectional view of a loading assembly in accordance with an embodiment of the present invention, including the compression member of FIG. 5, the support member of FIG. 6, and the constricting member of FIG. 25A.

FIG. 26 illustrates an assembled loading assembly 200' including the compression member 202 of FIG. 5, the support member 204 of FIG. 6 and the constricting member 600 of FIG. 25A. The compression member 202 and the support member 204 may be connected to one another as described above. With regard to the constricting member 600, at least the funnel portion 610 of the constricting member 600 is positioned within the opening 218 of the tubular extension 216 of the compression member 202.

FIGS. 27A and 27B show a constricting member 700 according to another embodiment of the present invention. The constricting member 700 has the same purpose as the constricting members 300 and 600 described above, and may be made of the same materials. The constricting member 700 may include a tubular member 702 having a central lumen 704 sized and shaped to slidingly receive at least a portion of the distal sheath 30 of the delivery device 10.

One end 706 of the tubular member 702 may include a funnel portion 710 to help compress the valve 100 during loading of the valve into the delivery device 10. The inner surface of the funnel portion 710 may taper from a larger diameter at an end of constricting member 700 to a smaller diameter where funnel portion 710 meets lumen 704.

The other end 707 of the tubular member 702 may have a funnel portion 709 which is substantially the same as funnel portion 710. The funnel portion 709 may facilitate the placement of constricting member 700 over the distal sheath 30 of the delivery device 10. The lumen 704 of constricting member 700 between funnel portions 709 and 710 may have a substantially constant diameter along its length, sufficient in size to receive at least the distal sheath 30 of the delivery device 10.

FIG. 28 depicts an assembled loading assembly 200" including the compression member 202 of FIG. 5, the support member 204 of FIG. 6 and the constricting member 700 of FIG. 27A. The compression member 202 and the support member 204 may be connected to one another as described above. The outer diameter of the ends 706 and 707 of the constricting member 700 may be substantially similar to the outer diameter of the tubular extension 216 of the compression member 202. In such event, the funnel portions 709 and 710 will not fit within or over the tubular extension 216. Rather, the ends 706 or 707 of the constricting member 700 may simply abut the tubular extension 216 and not be connected to same.

Figure 29:
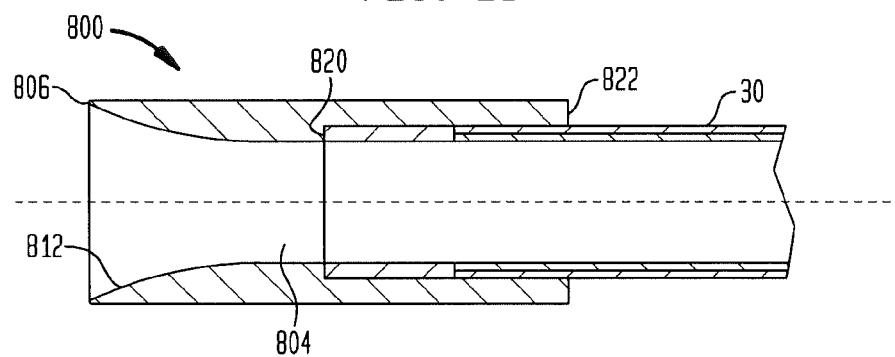
FIG. 29 is a longitudinal cross-sectional view of a constricting member according to an embodiment of the present invention placed over the distal sheath of the delivery device of FIG. 1.

FIG. 29 shows a constricting member 800 according to yet another embodiment of the present invention. The constricting member 800 may be used in conjunction with any of the compression members or support members described in the present disclosure. Again, the constricting member 800 has the same purpose as the constricting members described above, and may be made of the same materials. The constricting member 800 may be substantially cylindrical and have a central lumen 804 sized and shaped to slidingly receive at least a portion of the distal sheath 30 of the delivery device 10, as shown. At one end 822, the inner diameter of the constricting member 800 may be slightly larger than the outer diameter of the distal sheath 30 of the delivery device 10. This diameter may extend inwardly a distance from the end 822, at which point the inner diameter may decrease sharply, defining a step or shoulder 820 on the inner surface of the constricting member 800. From the shoulder 820 to the opposite end 806 of the constricting member 800, the inner surface 812 of lumen 804 gradually curves outwardly. The curved inner surface 812 of the constricting member 800 helps compress the valve 100 when the valve is loaded into the delivery device 10.

Figure 30:
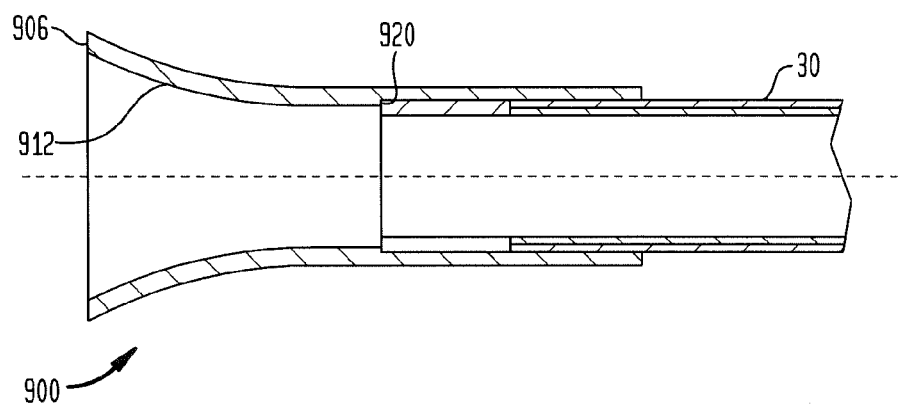
FIG. 30 is a longitudinal cross-sectional view of a constricting member according to another embodiment of the present invention placed over the distal sheath of the delivery device of FIG. 1.

FIG. 30 illustrates a constricting member 900 according to still a further embodiment of the present invention. The constricting member 900 is substantially similar to constricting member 800 described above. However, rather than having just the inner surface 912 of the constricting member gradually curve outwardly from a shoulder 920 to an end 906, both the inner and outer surfaces may curve outwardly in a horn configuration.

Figure 31:
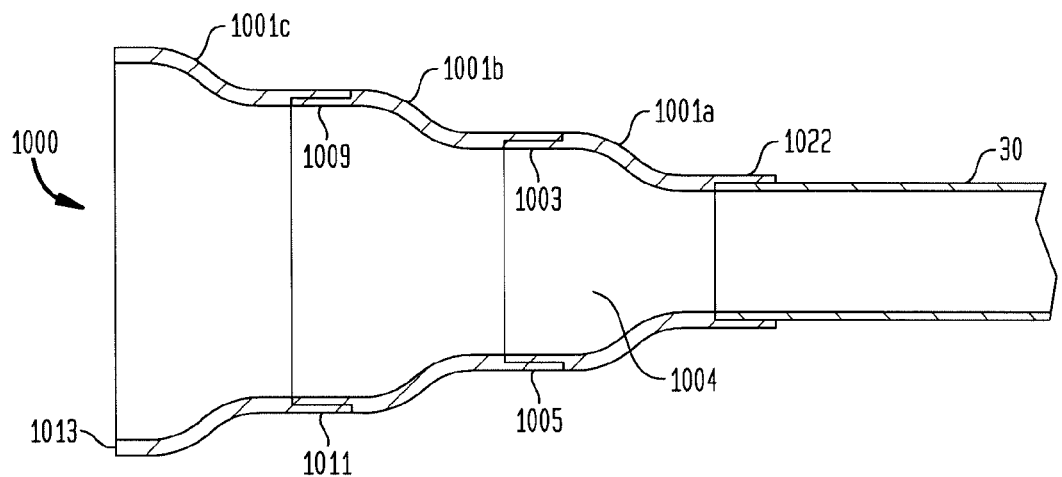
FIG. 31 is a longitudinal cross-sectional view of a constricting member according to a further embodiment of the present invention placed over the distal sheath of the delivery device of FIG. 1.

A constricting member 1000 in accordance with yet another embodiment of the present invention is shown in FIG. 31. The constricting member 1000 may be used in conjunction with any of the compression members and support members described in the present disclosure, and may be made of the same materials as the other constricting members described above. The constricting member 1000 may be made of a plurality of interlocking sections or segments 1001a, 1001b, 1001c. Although FIG. 31 depicts a constricting member 1000 with three interlocking sections 1001a, 1001b, 1001c, the constricting member may include two or more interlocking sections. The interlocking sections increase in diameter from the section 1001a having the smallest diameter to the section 1001c having the largest diameter. The interlocking section 1001a has an end portion 1022 which may have a substantially uniform inner diameter slightly larger than the diameter of the distal sheath 30 of the delivery device 10. Accordingly, the end portion 1022 of the interlocking section 1001a may receive at least a portion of the distal sheath 30. The interlocking section 1001a may increase in diameter in a gradual or step-wise fashion from the end portion 1022 to the opposite end 1003 thereof.

The end 1003 of interlocking section 1001a is connected to an end 1005 of a next adjacent interlocking section 1001b. This connection may be made using any suitable means, including adhesive, fasteners or a snap-fit connection. The interlocking section 1001b may increase in diameter in a gradual or step-wise fashion from the end 1005 to its opposite end 1009.

The end 1009 of interlocking section 1001b is connected to an end 1011 of a next adjacent section 1001c using any of the means noted above for connecting interlocking sections 1001a and 1001b together. The interlocking section 1001c may increase in diameter in a gradual or step-wise fashion from the end 1011 to its opposite end 1013. Hence, when assembled together, interlocking sections 1001a, 1001b and 1001c collectively define an interior space 1004 which decreases in diameter from end 1013 to end portion 1022 to help compress the valve 100 as it is loaded into the delivery device 10.

Figure 32:
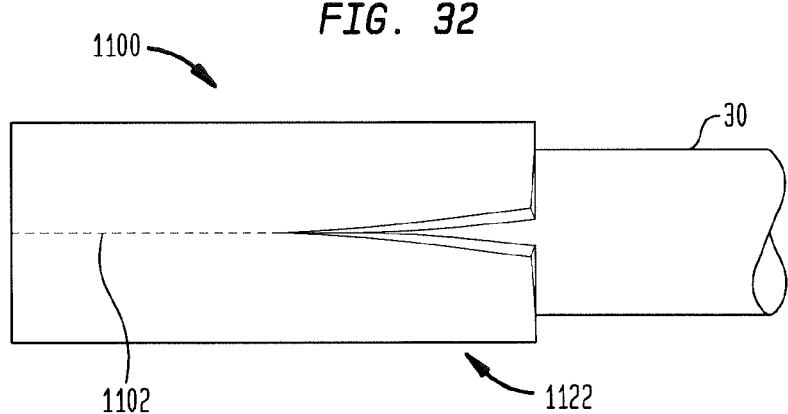
FIG. 32 is a side elevation of a constricting member according to yet a further embodiment of the present invention placed over the distal sheath of the delivery device of FIG. 1.

FIG. 32 shows a splittable constricting member 1100 according to another embodiment of the present invention. The constricting member 1100 may be used in conjunction with any of the compression members and support members described in the present disclosure, and may be sized and shaped to receive the distal sheath 30 of the delivery device 10. In particular, the constricting member 1100 includes one or more tear lines 1102 extending in the longitudinal direction along at least a portion of its length. The tear lines 1102 allow a user to split the constricting member 1100, thereby facilitating removal of the constricting member from the distal sheath 30 of the delivery device. An end portion 1122 of the tear lines 1102 may already be torn to separate an end of the constricting member 1100 into two or more portions, enabling a user to grab one edge and split the remainder of the constricting member along the tear lines.

Figure 33:
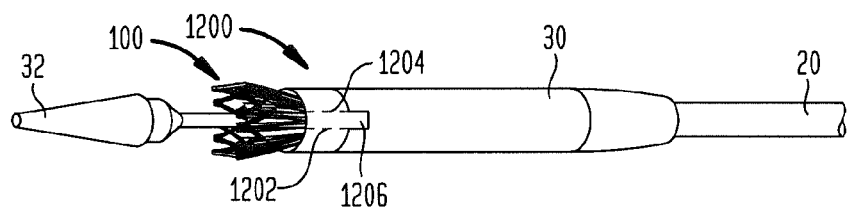
FIG. 33 is a cross-sectional side view of a constricting member according to an embodiment of the present invention placed over the distal sheath of the delivery device of FIG. 1.

Referring to FIG. 33, a splittable constricting member 1200 according to an alternate embodiment of the present invention may be sized and shaped to receive at least a portion of the distal sheath 30. The constricting member 1200 includes at least two tear lines 1202 and 1204 extending in the longitudinal direction along at least a portion of its length. The tear lines 1202 and 1204 may extend along the entire length of the constricting member 1200 or along a portion thereof, and may be oriented substantially parallel to one another. A pull tab 1206 may be provided to facilitate the tearing of the constricting member 1200 along the tear lines 1202 and 1204.

Figure 34:
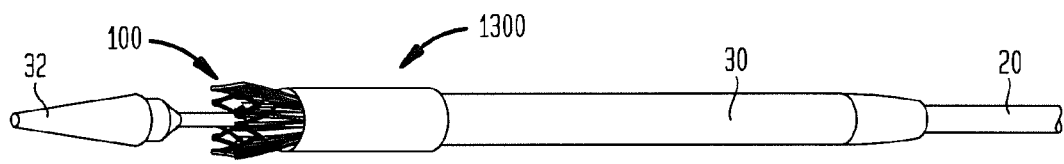
FIG. 34 is a side elevation of a constricting member according to still another embodiment of the present invention placed over the distal sheath of the delivery device of FIG. 1.

A constricting member 1300 in accordance with another embodiment of the present invention is shown in FIG. 34. The constricting member 1300 may be wholly or partly made of a substantially rigid material, such as a rigid metal or polymer, and includes a lumen (not shown) extending therethrough and dimensioned to receive at least a portion of the distal sheath 30.

Figure 35:
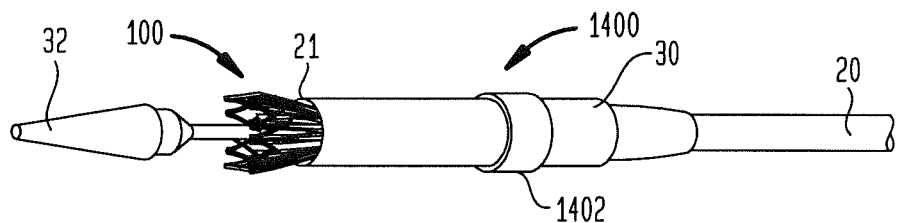
FIG. 35 is a perspective view of a constricting member according to still a further embodiment of the present invention placed over the distal sheath of the delivery device of FIG. 1.

With reference to FIG. 35, a constricting member 1400 in accordance with a further embodiment of the present invention may be in the form of a ring or collar 1402 formed from a substantially rigid material, such as a rigid metal or polymer. The ring 1402 may include an axial bore (not shown) having an inner diameter that is slightly larger than the outer diameter of the delivery sheath 30. When loading the valve 100 into the delivery device 10, the ring 1402 may be positioned about the distal end 21 of the distal sheath 30 to substantially prevent it from flaring.

Figure 36:
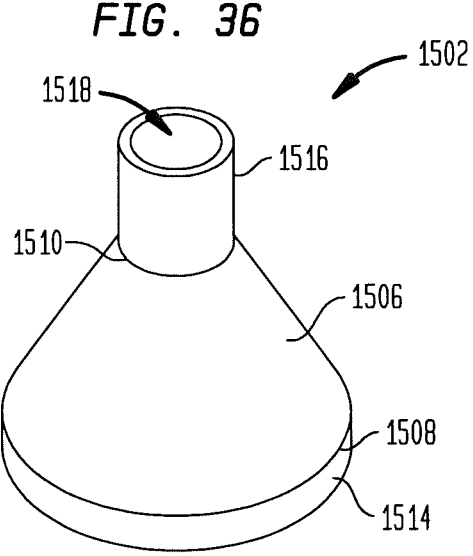
FIG. 36 is a perspective view of a compression member in accordance with another embodiment of the present invention.

FIG. 36 depicts a compression member 1502 in accordance with an alternate embodiment of the present invention. The compression member 1502 is similar to compression member 202 described above, and includes a funnel 1506 having a substantially frusto-conical shape with a large diameter at a first end 1508 and a smaller diameter at a second end 1510. The diameter of the funnel 1506 may decrease uniformly from the first end 1508 to the second end 1510 to compress the valve 100 as it is advanced through the compression member 1502. The compression member 1502 is preferably made of a substantially rigid material, and may be wholly or partly made of a transparent material, such as polycarbonate or acrylic, to allow viewing of the valve 100 as it is advanced therethrough during a loading procedure.

An annular rim 1514 may extend from the first end 1508 of the funnel 1506 for joining the compression member 1502 to a support member, such as support member 1504 described below. A tubular extension 1516 may project from the second end 1510 of the funnel 1506. The tubular extension 1516 has an opening 1518 therethrough in communication with the interior of the funnel 1506. The opening 1518 is sized and shaped to receive the distal sheath 30 of the delivery device 10 therein. The cross-section of the tubular extension 1516 is preferably substantially circular, but may be oblong, oval, elliptical, or polygonal.

Figure 37:
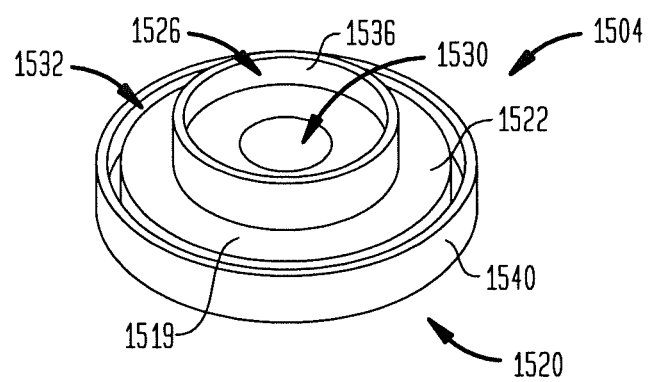
FIG. 37 is a perspective view of a support member according to an embodiment of the present invention for use with the compression member of FIG. 36.

The support member 1504 for use with the compression member 1502 is shown in FIG. 37. The support member 1504 is preferably made in whole or in part of a substantially rigid material, and includes a body 1519 having a substantially flat or planar bottom support surface 1520 and a substantially flat or planar top surface 1522. An outer wall 1540 may be spaced from top surface 1522 so as to define an annular slot 1532, sized and shaped to receive at least a portion of the rim 1514 of the compression member 1502 in a friction fit relationship.

Body 1519 has a generally cylindrical through bore 1530 which is sized and shaped to receive at least a portion of the tip 32 of the delivery device 10 therein. An inner wall 1536 may project upwardly from the top surface 1522 of body 1519 concentrically with the bore 1530 and between the bore and the outer wall 1540. The inner wall 1536 defines a recess 1526 having a diameter and a depth sufficient to receive at least a portion of the annulus section 106 of the stent 102 in an expanded state.

Figure 38:
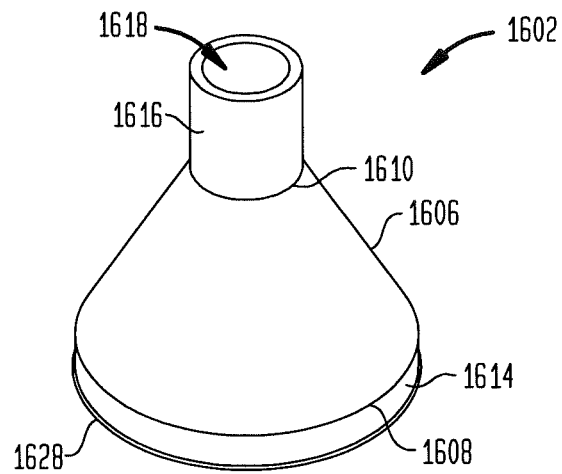
FIG. 38 is a perspective view of a compression member according to a still further embodiment of the present invention.

FIG. 38 shows an alternate embodiment of a compression member 1602 which is substantially similar to the compression member 1502 described above. Thus, the compression member 1602 includes a funnel 1606 having a first end 1608, a second end 1610, a rim 1614, and a tubular extension 1616 having an opening 1618. In addition, the compression member 1602 includes an enlarged bead or lip 1628 formed on the free edge of the rim 1614. The bead 1628 may extend continuously along the entire free edge of the rim 1614, along a portion of the free edge of the rim, or may be segmented so as to extend intermittently along the free edge of the rim.

Figure 39:
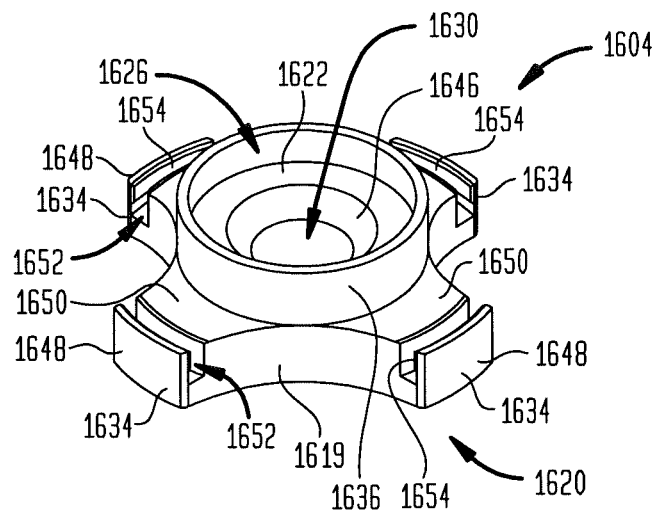
FIG. 39 is a perspective view of a support member according to an embodiment of the present invention for use with the compression member of FIG. 38.

FIG. 39 illustrates a support member 1604 for use with the compression member 1602 of FIG. 38. The support member 1604 preferably is made in whole or in part of a substantially rigid material and includes a body 1619 having a substantially flat or planar bottom support surface 1620 and a substantially flat or planar top surface 1622. Body 1619 has a generally cylindrical through bore 1630 which is sized and shaped to receive at least a portion of the tip 32 of the delivery device 10 therein. A chamfer 1646 may be formed at the intersection of bore 1630 with the top surface 1622. A wall 1636 may project upwardly from the top surface 1622 of body 1619 concentrically with the bore 1630 and spaced outwardly therefrom. The wall 1636 defines a recess 1626 having a diameter and a depth sufficient to receive at least a portion of the annulus section 106 of the stent 102 in an expanded state.

The support member 1604 may further include a plurality of locking arms 1634 extending radially outward from the body 1619. Although FIG. 39 shows a support member having four locking arms 1634, the support member 1604 may have a greater or lesser number of such locking arms. Each locking arm 1634 has a substantially flat top surface 1650, which may be substantially coplanar with the top surface 1622 of the body 1619. Near their free ends 1648, each locking arm 1634 may include a curved slot 1652, with all of the curved slots 1652 lying in the circumference of a single circle. Each locking arm 1634 may further include an inwardly projecting flange 1654 which partially occludes the top opening to its respective slot 1652. Slots 1652 are sized and shaped to receive at least a portion of the rim 1614 of the compression member 1602. In order to lock the compression member 1602 to the support member 1604, the rim 1614 may be forcibly inserted into slots 1652. The engagement of bead 1628 with the flanges 1654 will prevent the rim 1614 from escaping the slots 1652, and will therefore make it difficult for the compression member and the support member to become uncoupled.

Figure 40:
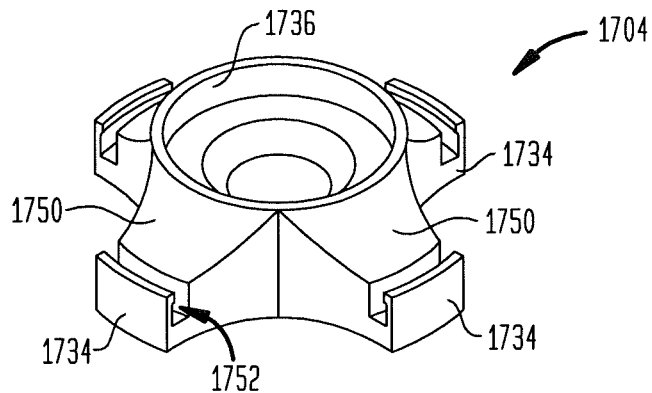
FIG. 40 is a perspective view of a support member according to another embodiment of the present invention for use with the compression member of FIG. 38.

FIG. 40 illustrates a support member 1704 which is a variant of support member 1604, and which may also be used with the compression member 1602. Rather than having substantially flat top surfaces as in the support member 1604, the locking arms 1734 of support member 1704 have top surfaces 1750 which are curved concavely from slots 1752 to the top edge of wall 1736.

Figure 41:
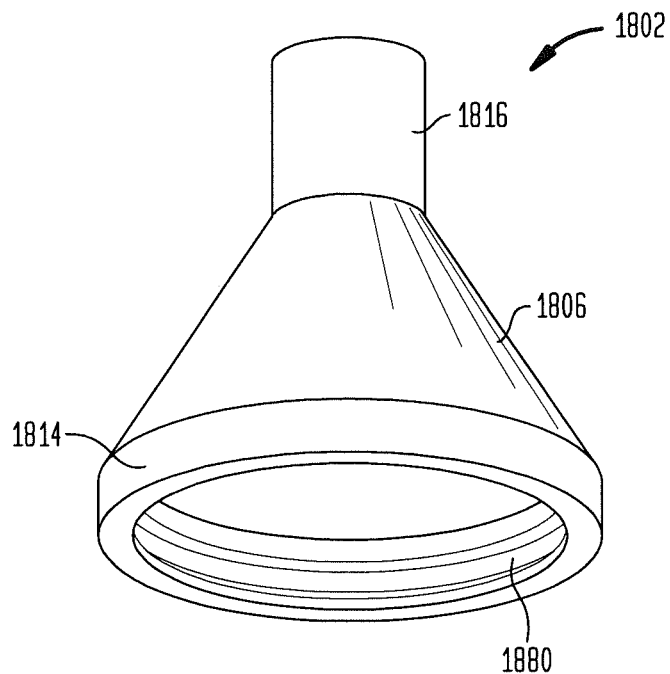
FIG. 41 is a perspective view of a compression member according to yet another embodiment of the present invention.
Figure 42:
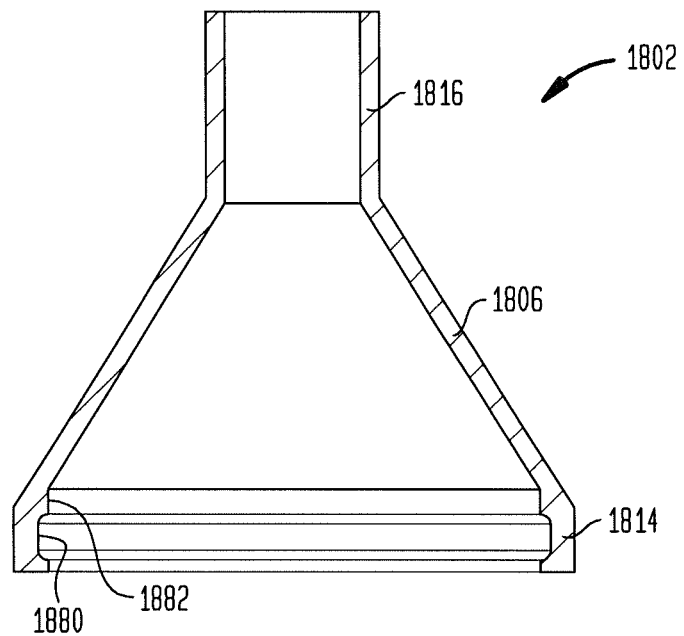
FIG. 42 is a longitudinal cross-sectional view of the compression member of FIG. 41.

FIGS. 41 and 42 show a compression member 1802 according to a further embodiment of the present invention. The compression member 1802 is similar to the compression member 1602 and may be formed of the same materials as the other compression members described above. Thus, the compression member 1802 includes a tubular extension 1816, a funnel 1806, and a rim 1814. The rim 1814 may include an internal groove 1880 formed on an inner surface 1882 thereof.

The internal groove 1880 may extend continuously along the entire length of the rim 1814, along a portion of the rim, or may be segmented so as to extend intermittently along the rim.

Figure 43:
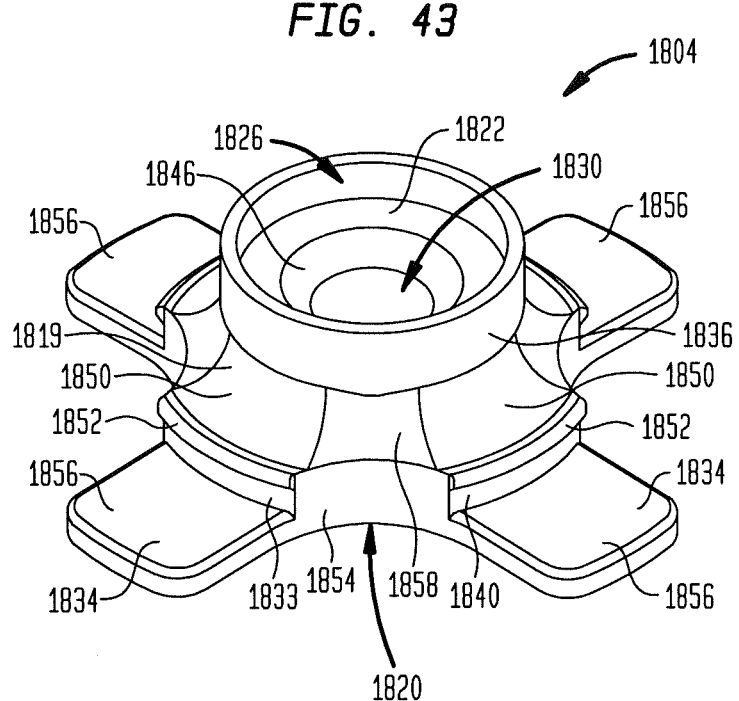
FIG. 43 is a perspective view of a support member according to another embodiment of the present invention.

FIG. 43 shows a support member 1804 according to the present invention which is particularly designed for use with the compression member 1802 of FIGS. 41 and 42. The support member 1804 includes a body 1819 having a substantially flat or planar bottom support surface 1820 and a substantially flat or planar top surface 1822. Body 1819 has an outer wall 1840 and a generally cylindrical through bore 1830 sized and shaped to receive at least a portion of the tip 32 of the delivery device 10. The intersection of bore 1830 with the top surface 1822 may be chamfered, as at 1846. An annular wall 1836 may project upwardly from the top surface 1822 of body 1819 concentrically with the bore 1830 and spaced outwardly therefrom so as to define a recess 1826 having a diameter and a depth sufficient to receive at least a portion of the annulus section 106 of the stent 102 in the expanded state.

The outer wall 1840 of body 1819 does not extend continuously around the body, but rather is interrupted by a plurality of inwardly curved indentations 1854 which divide the outer wall into a plurality of outer wall segments 1833. In an exemplary embodiment, the support member 1804 may have four such indentations 1854 defining four outer wall segments 1833. Indentations 1854 facilitate the grasping of support member 1804. Between the top of each outer wall segment 1833 and the bottom of wall 1836, body 1819 may have a concave surface 1850. Surfaces 1850 may alternate with similar concave surfaces 1858 extending between the top of each indentation 1854 and the bottom of wall 1836, thus defining a scalloped surface extending around the entire periphery of body 1819.

A support plate 1834 projects radially outward from the bottom end of each outer wall segment 1833. The support plates 1834 may have a substantially flat top surface 1856, and preferably have bottom surfaces which are substantially coplanar with the bottom support surface 1820 of body 1819. At their top ends, outer wall segments 1833 each include an outwardly projecting lip 1852 having an inclined top surface and a flat bottom surface spaced from the top surface 1856 of a respective support plate 1834. In use, the lips 1852 are adapted to be securely received in the groove 1880 of the compression member 1802 so as to lock the compression member to the support member 1804.

Figure 44:
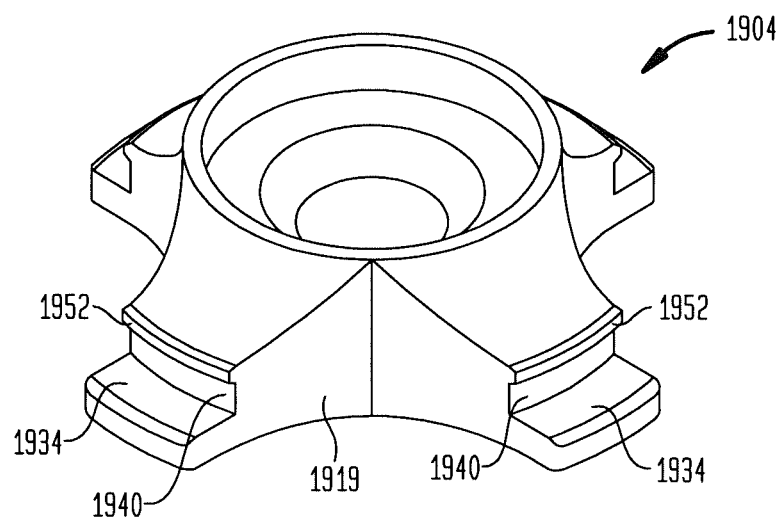
FIG. 44 is a perspective view of a support member according to a further embodiment of the present invention.

FIG. 44 shows another support member 1904 according to the present invention and particularly designed for use with the compression member 1802. The support member 1904 is substantially similar to the support member 1704 of FIG. 40, but has the locking structure of FIG. 43. That is, support member 1904 has a support plate 1934 projecting radially outward from the bottom of each outer wall segment 1940, and a lip 1952 projecting radially outward from the top of each outer wall segment. The lips 1952 have an inclined top surface and a flat bottom surface, and are sized and shaped to be securely received in the groove 1880 of the compression member 1802 to lock the compression member to the support member 1904. During use, the compression member 1802 can be locked to the support member 1904 by placing the rim 1814 of the compression member against the lips 1952 of the support member and pushing the members together so that the lips are pushed into the groove 1880 of the compression member.

Figure 45:
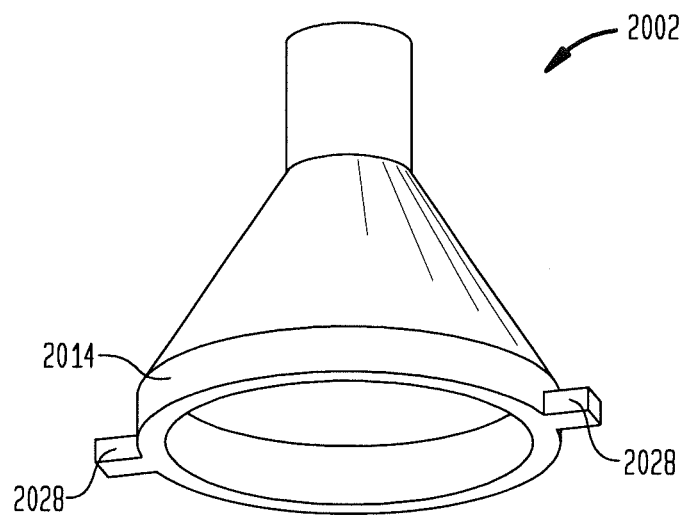
FIG. 45 is a perspective view of a compression member according to still another embodiment of the present invention.

FIG. 45 shows a compression member 2002 according to yet another embodiment of the present invention. The compression member 2002 is substantially similar to the compression member 1602 of FIG. 38. However, rather than bead 1628, compression member 2002 includes one or more tabs 2028 protruding radially outward from the rim 2014. While FIG. 45 shows two such tabs 2028, the compression member 2002 may have more or fewer tabs. Where the compression member 2002 has two tabs 2028, they preferably are disposed diametrically apart from one another. Where the compression member 2002 has more than two tabs 2028, they preferably are spaced substantially evenly apart along the rim 2014. The tabs 2028 may have any shape, including, for example, rectangular, cylindrical, triangular, elliptical, etc., capable of mating with the support member 2004 described below.

Figure 46:
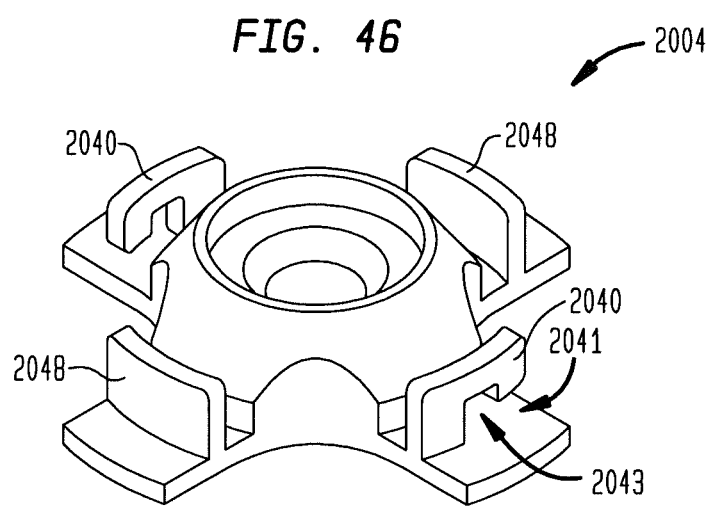
FIG. 46 is a perspective view of a support member according to yet a further embodiment of the present invention.

FIG. 46 shows the support member 2004 designed for use with the compression member 2002. The support member 2004 is similar to the support member 504 of FIG. 24. However, rather than having pins extending radially inward from outer walls 2048, a number of the outer walls are formed in the shape of a hook, as at 2040. The hooks 2040 have an open side 2041 and an upwardly extending recess 2043, both of which are sized and shaped to receive the tabs 2028 of the compression member 2002 for locking the compression member to the support member 2004. Although each of outer walls 2048 may be formed with a hook 2040, it will be understood that support member 2004 should have at least as many hooks as the compression member 2002 has tabs 2028. Furthermore, the hooks 2040 should be positioned around the periphery of supporting member 2004 so as to correspond with the positions of tabs 2028 on compression member 2002.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. An assembly for loading a self-expanding prosthetic heart valve into a delivery device, comprising:

a compression member having a longitudinal axis, a first open end with a first diameter, a second open end with a second diameter less than the first diameter, and a wall decreasing in diameter from the first open end to the second open end, the wall defining an open space adapted to receive the valve;

a support member having a longitudinal axis, a base and a recess extending along the longitudinal axis and adapted to receive an end of the valve, the support member and the compression member being movable relative to one another between an initial position in which the base of the support member is relatively far from the first open end of the compression member and an operative position in which the base of the support member is relatively close to the first open end of the compression member, wherein movement of the support member and the compression member from the initial position to the operative position pushes the valve through the open space such that the valve is radially compressed by the tapered wall of the compression member as the valve advances through the open space; and a constricting member separable from the compression member and having a first end, a second end, an end member on the second end, and an elongated tubular portion having a lumen between the first end and the second end, the end member having a free end and another end connected to the tubular portion, the end member having a first diameter at the free end, a second diameter less than the first diameter at the another end, and a wall decreasing in diameter from the free end to the another end.

2. The assembly according to claim 1, wherein the lumen of the elongated tubular portion has a substantially constant diameter sized to slidably receive at least a distal sheath of the delivery device.

3. The assembly according to claim 1, further comprising a tubular extension on the second open end of the compression member, the tubular extension having a lumen therethrough, the lumen having a diameter which is substantially equal to the second diameter.

4. The assembly according to claim 3, wherein the second end of the constricting member is sized and shaped for assembly to the tubular extension.

5. The assembly according to claim 1, wherein the wall of the compression member decreases in diameter uniformly from the first open end to the second open end.

6. The assembly according to claim 1, further comprising a locking assembly for locking the compression member to the support member.

7. The assembly according to claim 6, wherein the locking assembly includes a male connecting member on one of the support member or the compression member, and a female connecting member on the other of the support member or the compression member for mating with the male connecting member.

8. The assembly according to claim 7, wherein the male connecting member includes a plurality of pins extending in radial directions from the longitudinal axis of the one of the support member or the compression member, and the female connecting member includes a plurality of features on the other of the support member or the compression member adapted to mate with the plurality of pins.

9. The assembly according to claim 1, wherein the support member has a through bore extending along the longitudinal axis of the support member, the through bore being sized to receive a tip of the delivery device therethrough.

10. The assembly according to claim 1, further comprising
a tubular extension on the second open end of the compression member, the tubular extension having a lumen therethrough, the tubular extension being engagable in an assembled position with the end member of the constricting member; and
a first seal interposed between the end member of the constricting member and the tubular extension of the compression member in the assembled position.

11. The assembly according to claim 10, further comprising a second seal disposed in the lumen of the elongated tubular portion of the constricting member.

12. The assembly according to claim 1, wherein the constricting member further includes another end member on the first end thereof, the another end member having a free end and another end connected to the tubular portion, and the another end member having a first diameter at the free end, a second diameter less than the first diameter at the another end, and a wall decreasing in diameter from the free end to the another end.

13. The assembly according to claim 1, wherein the constricting member includes a plurality of interlocking segments connected to one another, each of the interlocking segments having a first segment end with a first diameter, a second segment end with a second diameter greater than the first diameter, and a segment wall increasing in diameter from the first segment end to the second segment end, the interlocking segments being connected together in series with the second segment end of one interlocking segment connected to the first segment end of a next adjacent interlocking segment.

14. The assembly according to claim 13, wherein the diameter of the wall increases in step-wise fashion.

15. The assembly according to claim 13, wherein the diameter of the wall increases uniformly from the first end to the second end.

16. The assembly according to claim 1, further comprising at least one tear line extending in a longitudinal direction between the first end and the second end of the constricting member for splitting the constricting member in the longitudinal direction.

17. The assembly according to claim 7, wherein the female connecting member includes an annular groove extending along an inner surface of the first open end of the compression member, and the male connecting member includes a plurality of locking tabs on the support member adapted to engage the annular groove of the compression member so as to connect the support member to the compression member.

18. The assembly according to claim 7, wherein the male connecting member includes an annular rim extending from the first open end of the compression member, and the female connecting member includes an annular slot on the support member sized to receive the rim so as to connect the compression member to the support member.

19. The assembly according to claim 6, wherein the locking assembly includes a bead extending along an outer periphery of the first open end of the compression member and locking tabs on the support member, the locking tabs being configured to engage the bead of the compression member so as to connect the support member to the compression member.

20. The assembly according to claim 1, wherein the second end of the constricting member is sized to receive the compressed valve from the second open end of the compression member.

* * * * *